(12) United States Patent
Lee et al.

(10) Patent No.: US 10,543,134 B2
(45) Date of Patent: Jan. 28, 2020

(54) BAND-FASTENED CONVENIENCE-PACKAGING FOR STORING ABSORBENT PERSONAL CARE ARTICLES

(71) Applicant: Kimberly-Clark Worldwide, Inc., Neenah, WI (US)

(72) Inventors: HyeJin Lee, Seoul-si (KR); SeongDae Roh, Yongin-si (KR); JongSoo Lee, Yongin-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 140 days.

(21) Appl. No.: 15/770,908

(22) PCT Filed: Oct. 30, 2015

(86) PCT No.: PCT/US2015/058392
§ 371 (c)(1),
(2) Date: Apr. 25, 2018

(87) PCT Pub. No.: WO2017/074439
PCT Pub. Date: May 4, 2017

(65) Prior Publication Data
US 2018/0353354 A1 Dec. 13, 2018

(51) Int. Cl.
*A61F 13/551* (2006.01)
*B65D 33/24* (2006.01)
(Continued)

(52) U.S. Cl.
CPC .... *A61F 13/55145* (2013.01); *A61F 13/5511* (2013.01); *A61F 13/5514* (2013.01);
(Continued)

(58) Field of Classification Search
CPC .......................... A61F 13/55145; A61F 13/15; A61F 13/5511; A61F 13/5514; A61F 13/84;
(Continued)

(56) References Cited

U.S. PATENT DOCUMENTS 3,394,715 A * 7/1968 Sachs ..................... B65D 75/52
132/289
4,286,639 A * 9/1981 Murphy ................ A61F 15/001
150/131
(Continued)

FOREIGN PATENT DOCUMENTS

CA 2109782 5/1995
CN 202010240 U 10/2011
(Continued)

*Primary Examiner* — Rafael A Ortiz
(74) *Attorney, Agent, or Firm* — Kimberly-Clark Worldwide, Inc.

(57) ABSTRACT

A band-fastened packaging for containing absorbent articles includes a pocket component for housing the articles. The pocket component includes a front and back wall, with at least the front wall defining an opening into the pocket component. At least the front and back walls form a packaging closed end. A packaging flap is hingedly connected to the back wall for covering the opening, the packaging flap including a flap wall having an outermost flap wall edge. A band-fastener is attached to the outermost flap wall edge. The band-fastener is capable of separating from the outermost flap wall edge between two spaced-apart points, and includes a flap-facing inner edge. The packaging closed end may be inserted between the outermost flap wall edge and band-fastener, flap-facing inner edge in order to maintain the packaging in a closed configuration.

20 Claims, 9 Drawing Sheets

(51) Int. Cl.
*A61F 13/84* (2006.01)
*B65D 77/06* (2006.01)
*B65D 77/12* (2006.01)
*B65D 75/52* (2006.01)

(52) U.S. Cl.
CPC .............. *A61F 13/84* (2013.01); *B65D 75/52* (2013.01); *B65D 77/06* (2013.01); *B65D 77/12* (2013.01); *B65D 33/243* (2013.01)

(58) Field of Classification Search
CPC . A61F 13/551; B65D 75/52; B65D 2075/362; B65D 2075/363; B65D 77/12; B65D 33/243; B65D 33/24
USPC ....... 206/440, 210, 286, 720, 438, 441, 494, 206/39.7, 1.5, 38, 233, 581, 823, 812; 383/84–86, 98, 99, 86.1, 86.2, 62, 42; 150/118, 127, 131, 149, 152
See application file for complete search history.

(56) References Cited

U.S. PATENT DOCUMENTS

| | | | |
|---|---|---|---|
| 4,564,108 A | | 1/1986 | Widlund |
| 5,392,974 A | * | 2/1995 | Johnson-Rabbett ...... A45F 5/02 206/278 |
| 5,941,641 A | * | 8/1999 | Kinigakis ............. A24F 23/02 206/260 |
| 6,041,928 A | * | 3/2000 | Jousinen ............. A61F 13/5514 206/440 |
| D474,680 S | | 5/2003 | Ling |
| 6,601,706 B2 | | 8/2003 | McManus |
| 6,635,039 B1 | | 10/2003 | Levy |
| 6,820,799 B2 | | 11/2004 | Makofsky |
| 7,178,671 B2 | | 2/2007 | Nichols |
| 7,181,893 B2 | | 2/2007 | Snell |
| D544,705 S | | 6/2007 | Zawacki |
| 7,942,857 B2 | * | 5/2011 | Chicoine ............. A61F 13/5514 206/440 |
| 8,074,801 B2 | | 12/2011 | Slayton |
| D651,790 S | | 1/2012 | Groves |
| 8,172,084 B2 | | 5/2012 | Goodrich et al. |
| 8,398,306 B2 | | 3/2013 | Kinigakis |
| 8,899,418 B2 | | 12/2014 | Francis |
| 2002/0084203 A1 | | 7/2002 | Cottingham |
| 2002/0153271 A1 | * | 10/2002 | McManus ......... A61F 13/47209 206/440 |
| 2003/0023217 A1 | | 1/2003 | McManus |
| 2003/0102239 A1 | | 6/2003 | Beard |
| 2005/0121349 A1 | | 6/2005 | Robert Hodges |
| 2005/0261651 A1 | | 11/2005 | Lima |
| 2006/0074390 A1 | | 4/2006 | Price |
| 2006/0142720 A1 | * | 6/2006 | Zander ................ A61F 13/5514 604/385.02 |
| 2007/0073255 A1 | | 3/2007 | Thomas |
| 2007/0241018 A1 | | 10/2007 | Forte |
| 2011/0095021 A1 | | 4/2011 | Clough |
| 2012/0099808 A1 | | 4/2012 | Washington |

FOREIGN PATENT DOCUMENTS

| | | |
|---|---|---|
| EP | 0419770 A1 | 4/1991 |
| EP | 1357877 B1 | 3/2011 |
| GB | 961178 A | 6/1964 |
| JP | 5279564 A2 | 10/1993 |
| JP | 2015066244 A2 | 4/2015 |
| KR | 300740937 S | 4/2014 |

\* cited by examiner

BAND-FASTENED CONVENIENCE-PACKAGING FOR STORING ABSORBENT PERSONAL CARE ARTICLES

FIELD OF THE INVENTION

The present invention is generally directed to packaging for absorbent personal care articles. In particular, the present invention is directed to portable and reclosable packaging for storing multiple absorbent personal care articles (at least some of which may be individually-wrapped), which packaging may be used as a convenience to easily transport a relatively small amount of such absorbent personal care articles in a discrete fashion.

BACKGROUND OF THE INVENTION

Absorbent personal care articles, such as feminine-care pads, napkins, and panty liners, and adult-care absorbent inserts (for undergarments) and absorbent pants, are frequently offered for bulk-volume sale as multiple individually-wrapped articles (each forming an inner package) contained within a single outer enclosure, so as to help preserve the cleanliness of such articles prior to use. For example, at least one compressed stack or row of individually-wrapped articles (i.e. each article in its own individual pouch or wrapper) are typically packed within either an outer-box, carton, or flexible-material container (hereinafter all referred to as "outer packaging"), such as a film, nonwoven, laminate, or foil-based bag. The individual wrappers themselves are typically also made from a flexible film, nonwoven sheet, or laminate of the two. Such outer packaging may include a reclosable flap to cover an opening in the packaging, such as for example, those flaps illustrated in U.S. Pat. No. 5,699,911 to Joseph et al. and in international patent publication WO2014/080878 to Kashiwagi et al.

More often than not, such outer packaging contains multiple stacks of wrapped articles. Such outer packaging is frequently stored in a consumer's bathroom cabinet or pantry, and is usually too large to be discretely transported on a consumer's person for dispensing such articles as needed. As a result of such size limitations of the outer packaging, and consumers' desire to discretely transport a relatively smaller number of absorbent articles at-a-time when away from home, a variety of more portable, "convenience" packaging designs have been developed. Such "convenience" packaging may resemble a wallet, and come initially with the articles stored inside. Such "convenience" packaging may also be repetitively restocked with articles taken from larger outer packaging, as the contents become depleted over time. Such "convenience" packaging designs protect such articles from contaminants in the surrounding environment, and maintain a level of organization of the articles, rather than the alternative of having them scattered about in a user's pockets, purse, or other transporting bag.

The "convenience" packaging, typically in the form of pouches with resealable adhesive flaps, are formed from flexible materials such as film or nonwoven sheet materials. For example, as seen in European Patent 1357877B1 to Ling et al., a resealable pouch is described for keeping a manageable number of individually-wrapped absorbent articles discretely in a single location, for storage typically within a consumer's pocket or purse. Such resealable pouch offers an alternative to such articles being spread loosely about, as such disorganization may eventually lead to article soiling from surrounding cosmetics or sundries, or even worse, may lead to article damage. Such protective pouch is often formed from an opaque and sometimes ornamentally-colored sheet material, so as to be emotionally uplifting, and so that the actual contents cannot be easily determined through the pouch, from casual observation of a passerby. It has been found that consumers prefer such stored articles also to be individually wrapped, despite the fact that they are also stored in the outer resealable pouch, in order to provide an extra level of protection from contaminants in the consumer's environment.

Despite being beneficial for and desired by consumers, in use such adhesively resealable pouches pose some operational challenges. For instance, such pouches require adhesively fastening and unfastening an envelope-style flap each time a new article from the pouch is needed. Therefore, the outer pouch only works to maintain complete separation of individually-wrapped absorbent articles from their outside environment as long as the adhesive fastener remains viable. If after repeated opening (i.e. unsealing) and closing (i.e. sealing) of the flap, the pressure-sensitive adhesive fastener loses its tackiness, the individually-wrapped articles may become soiled (as a result of environmental contaminants penetrating the packaging through the open flap) or actually fall from the packaging through the open flap. Additionally, unsightly contaminants and dirt from a consumer's environment may become stuck to the adhesive of the pouch flap. Further, restocking of packaging having adhesive flaps may pose challenges, as the adhesive may inadvertently stick to the absorbent articles themselves, as they are being replaced in the packaging for later use. Finally, such limited-life adhesive frequently adds significant manufacturing complexity and expense to the manufacturing costs of the packaging. Therefore, there is a need for "convenience" absorbent article packaging, which provides for extended use of a reclosable flap during repeated opening and closing operations, and without the use of costly adhesive. There is a further need for a convenience absorbent article packaging which may be easily restocked with individual absorbent articles, as packaging contents become depleted.

While other types of reclosable closure mechanisms are available for use on convenience packaging, such as for example, zipper-like devices, tie-knot devices, button and loop-type devices, and mechanical fasteners such as hook and loop materials, such structures also require more complex manufacturing steps for implementation, and add significant expense to the overall packaging cost. There is therefore a need for an alternative closure mechanism which may be easily understood by consumers and used on absorbent article "convenience" packaging, and which does not add significantly to overall packaging costs. There is a further need for active-consumer, "on-the-go" style packaging, which packaging may be easily transported, and which may be repeatedly opened and closed despite diverse environmental conditions, such as those which may be encountered during a consumer's exercise routine in a gym, aquatic facility, or outside a consumer's residence. There is also a need for such packaging which may be adjustably closed so as to accommodate an ever-changing amount of packaging contents over time.

SUMMARY OF THE INVENTION

A band-fastened packaging for containing absorbent articles includes a longitudinal dimension, a width dimension, and a thickness dimension. The packaging includes a pocket component for housing absorbent articles. The pocket component includes at least a front and back wall, with at least the front wall defining an opening into the pocket component and at least the front and back walls forming a packaging closed end. A packaging flap is hingedly connected to the back wall for folding over the opening. The packaging flap includes a flap wall having an outermost flap wall edge. A band-fastener is attached to the outermost flap wall edge at least at two spaced-apart attachment points. The band-fastener is capable of separating (moving apart) from the outermost flap wall edge between the at least two spaced-apart attachment points, and includes a flap-facing inner edge, such that the packaging closed end may be inserted between the two spaced-apart attachment points and also between the outermost flap wall edge and the band-fastener flap-facing inner edge, whereby the packaging flap may be held in place adjacent the packaging closed end in order to maintain the opening covered by the packaging flap until an absorbent article that may be contained within the band-fastened packaging is desired for use. In one embodiment, a few absorbent articles or individually-wrapped absorbent articles are contained within the packaging. In a second embodiment, multiple individually-wrapped absorbent articles are containing within the packaging.

In a further alternative embodiment of the band-fastened packaging, the band-fastener is attached to the outermost flap wall edge along a frangible seam between the outermost flap wall edge and the band-fastener flap facing inner edge. The frangible seam is selected from the group consisting of a line of perforation, line of weakness, and a combination thereof. In yet another alternative embodiment, the band-fastener is separated from the outermost flap wall edge by a distance of between about 1 and 10 mm, thereby forming a spatial gap between the two attachment points, and between the outermost flap wall edge and the band-fastener flap-facing inner edge. In still another alternative embodiment, the band-fastener is formed from either a stretchable material, an elastic material, a tissue material, a metal, a polymeric material or a flexible material. Such band-fastener may be formed from the same material as the flap wall and/or packaging (such as the pocket component walls) or from a different material.

In still a further alternative embodiment, the front wall entirely defines the opening into the pocket component. In another alternative embodiment, the front and back walls together define the opening into the pocket component, with only the front wall having an exposed edge. In another alternative embodiment, the front wall and back wall have two different lengths.

In still another alternative embodiment, the band-fastener includes a width dimension and includes a sealed edge along its full width dimension. In another embodiment, the back wall is either integral with the flap wall, or a separate layer from the flap wall (but which separate layer is attached to the back wall, such as by ultrasonic, thermal, or adhesive bonding). If a first feature within the packaging is integral with a second feature (such as the flap wall and back wall, or flap wall and band-fastener), it is in one embodiment, formed from the same material as the second feature. In some instances, a cutting, slitting, or aperturing process step may be used to separate a single sheet into two portions (forming the two features), such as may be done with the formation of a band-fastener from the flap wall.

In yet another alternative embodiment of the invention, the band-fastener is integral with the flap wall, such as being attached to it at least at two points, and in another alternative embodiment, at multiple points along the band-fastener width. In another alternative embodiment, the band-fastener is of uniform length across its entire width dimension.

In still a further alternative embodiment, the packaging includes individually-wrapped absorbent articles contained within the pocket component, wherein the individually-wrapped absorbent articles are folded absorbent articles that are wrapped in wrappers having two opposing sealed edges and two opposing folded edges, and further wherein the individually-wrapped absorbent articles are placed within the band-fastened packaging such that the wrapper sealed edges are parallel with the band-fastened packaging longitudinal dimension. In another embodiment, the individually-wrapped absorbent articles contained within the pocket component number between 2 and 20, alternatively between 2 and 10, alternatively, either 5, 6, or 7. In still a further alternative embodiment, at least one of the individually-wrapped absorbent article varies from another individually-wrapped absorbent article in the packaging, such variation based on either article size, article absorbency, article aesthetics, or article type. For example, such packaging contents may include two different types of absorbent articles, such as feminine care pads and liners, or adult care incontinence inserts and garments.

In another alternative embodiment of the invention, the packaging, or alternatively the pocket component and the packaging flap, are formed of substantially opaque materials such that contents contained within the pocket component which opening is covered by the packaging flap are not capable of article-type identification by a consumer with 20/20 vision, when viewing the packaging from a distance of one meter away.

In still another alternative embodiment, the band-fastener is of an elongated length. In still another alternative embodiment, the band-fastener is formed of an elastic material. In yet another alternative embodiment, the band-fastener is formed of a nonelastic material. In yet another alternative embodiment, the band-fastener is formed from an extensible material. In yet another alternative embodiment, the flap wall and band-fastener are both formed from the same material. In still another alternative embodiment, the flap wall is formed from either an elastic or extensible material.

In another alternative embodiment, the band-fastener, the flap wall outermost edge, and other peripheral side edges of the band-fastened packaging include ultrasonic bond areas (i.e. seal lines) or other forms of bonded areas. In yet another alternative embodiment, all exposed edges of the packaging include seal lines. In still another alternative embodiment, a seal line or bonded area forms a hinge-type fold line separating the pocket component from the flap wall. In another alternative embodiment, the front and back walls both define the opening. In still another embodiment, the band-fastener includes upon its surface, a secondary closure mechanism selected from the group consisting of adhesive, a tie knot, and a hook or loop fastener so as to further secure the packaging flap to the back wall while the packaging is in a closed configuration.

In yet another alternative embodiment, the packaging includes a transparent or translucent portion, such that individual wrappers of individually-wrapped articles contained within the band-fastened packaging can be seen through the transparent or translucent portion. In another alternative embodiment, the packaging includes visual cues to facilitate a consumer's operation of the band-fastened packaging.

BRIEF DESCRIPTION OF THE DRAWINGS

A full and enabling disclosure of the present invention is set forth more particularly in the remainder of the specification, including reference to the accompanying figures, in which.

DETAILED DESCRIPTION

Definitions

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

Figure 3:
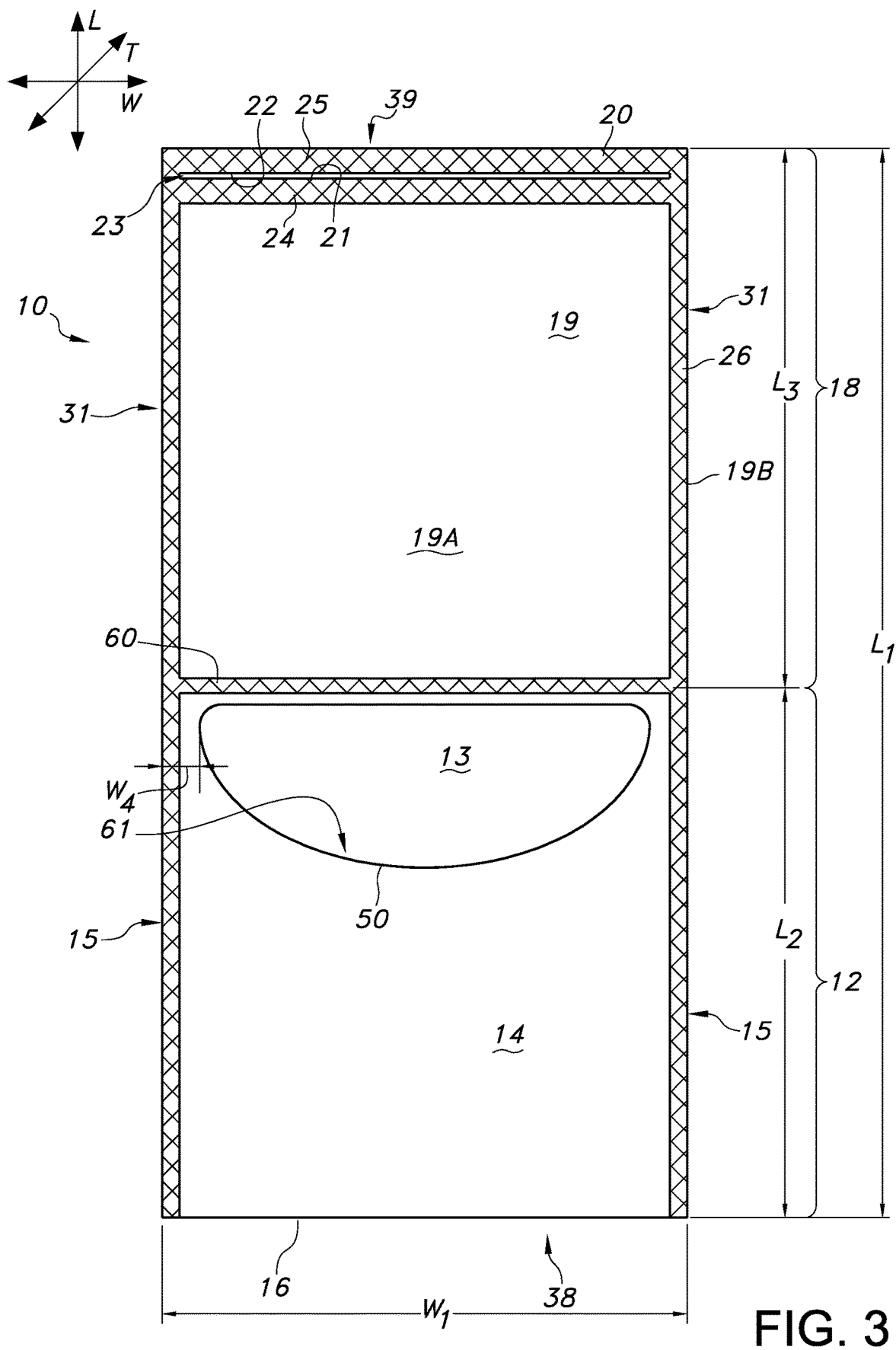
FIG. 3 illustrates a front (and opened) top plan view of an alternative embodiment of a reclosable, band-fastened convenience packaging for storing multiple personal care absorbent articles, said packaging shown in a generally flattened condition.

As used herein, the term "convenience" shall refer to a packaging format which is easily portable, such as for example, by being capable of fitting in a consumer's pocket, alternatively in a purse, overnight bag, carry-on bag, exercise bag (such as a draw-string bag), or a so-called "fanny" or waist pack. Desirably in a first embodiment, such packaging is capable of accommodating between 2 and 20 personal care absorbent articles, alternatively between 2 and 20 individually-wrapped personal care absorbent articles (such as folded personal care absorbent articles), alternatively between 2 and 10 individually-wrapped, folded personal care absorbent articles, alternatively, between 4 and 10 individually-wrapped, folded personal care absorbent articles. For the purposes of this disclosure, such personal care absorbent articles may encompass absorbent articles from one or more personal hygiene product categories, such as feminine care and adult incontinence care absorbent articles. In yet a further alternative embodiment, different absorbent articles from the same product category, such as for example, at least two different size or absorbency-level articles (such as a regular length sanitary pad and overnight size sanitary pad), alternatively, at least two aesthetically different articles, or alternatively, at least two different types of products such as panty liners and sanitary pads, or absorbent incontinence inserts and one or more absorbent garments (absorbent pants or diapers), are placed together within one such convenience packaging of the invention. In still a further alternative embodiment, such convenience packaging of the invention has an overall opened, extended and generally flattened length L1 (as seen in FIG. 3) upon a level flat surface (and without containing articles) of between about 70 and 300 mm, alternatively, between about 120 and 200 mm, an overall opened, extended and generally flattened width W1 upon a level flat surface (without containing articles) of between about 25 and 120 mm, alternatively, between about 50 and 90 mm, and an expanded thickness T1, T2 of between about 5 and 60 mm, alternatively, between about 15 and 45 mm. For the purposes of this disclosure, the term "expanded thickness" shall refer to the thickness of the closed packaging (flap fastened about packaging closed end) when it is filled with absorbent articles to its capacity, and without packaging or band-fastener rupture. Desirably, the packaging flap itself does not add much appreciable thickness to the overall expanded thickness dimension of the packaging, such as in one embodiment, less than 3 mm, alternatively, less than 1 mm. Furthermore, it is desirable in one embodiment, for the convenience packaging to be capable of being restocked with new absorbent article contents, once the initial contents have been depleted.

As used herein, the term "band" in connection with the term "band-fastener", shall refer to a strip-like structure having two lateral-most end regions, and which is attached to the outermost edge of a packaging flap wall at least at two separated points of the strip-like structure, two lateral-most end regions. Such band-fastener may be either an integral component of the packaging flap wall, situated adjacent to the flap wall outermost edge, or alternatively a non-integral component of the packaging flap, attached to the flap wall outermost edge. Such band-fastener is attached at least at its two lateral-most end regions to a portion of the flap wall, but may alternatively include a frangible seal along which the band-fastener is attached along its width, to the flap wall outermost edge at multiple points along the flap wall outermost edge width. Such band-fastener is capable of extending around a closed end of the packaging (by the action of the packaging closed end sliding through an opening between a band-fastener, flap-facing inner edge and an outermost edge of the flap wall), for maintaining a packaging flap in place about the packaging closed end and pocket component opening, and also for preventing the packaging flap from easily separating from the remainder of the packaging while such packaging is being transported by a consumer. In an alternative embodiment, the band-fastener has a uniform narrow length dimension L8 along its width, such as between about 1 and 30 mm, alternatively, between about 3 and 5 mm.

As used herein, the terms "nonwoven," "nonwoven fabric," and "nonwoven web" shall be interchangeable, and refer to a web having a structure of individual fibers or threads which are interlaid, but not in an identifiable manner as in a knitted fabric. Nonwoven fabrics or webs have been formed from many processes such as for example, meltblowing processes, spunbonding processes, coform processes, hydroentangling, and bonded carded web processes (such as thermal bonded carded webs or TBCW, and through-air bonded carded webs or TABCW). The terms may actually also encompass laminates of two or more individual nonwoven webs.

As used herein, the term "elastic" shall mean that property of a material or composite material (such as a laminate of two or more materials) that permits it to recover at least a portion of its original size and shape after removal of the force causing a deformation of the material. For example, in an elastic material, a portion of an elongation of the elastic material would shrink/recover upon removal of the elongation force.

As used herein, the term "stretchable" shall be interchangeable with the term "extensible" and shall mean that property of a material or composite material (such as a laminate of two or more materials) that permits it to elongate from at least a portion of its original size and shape without rupturing, and which, after removal of the force causing elongation of the material, does not shrink/recover from any of its elongation.

As used herein, the term "flexible material" shall refer to a sheet material such as a woven, nonwoven, polymeric or metal film, or paper material, which is capable of enclosing and bending around multiple absorbent articles without creating a seam or a rupture of the sheet material, unless by intention. Desirably, such flexible material is capable of being bonded to itself, such as by ultrasonic or thermal bonding. In an alternative embodiment, such flexible material is capable of being bonded to itself by the use of secondary materials, such as via adhesive, needle stitching, hydroentanglement, or staple bonding techniques.

EMBODIMENTS OF THE INVENTION

So as to provide a portable and reclosable packaging for conveniently storing a relatively small number of absorbent articles that may be needed by a consumer during a single day or over a period of a few days, a packaging configuration has been developed which includes a packaging pocket component, a packaging flap having a flap wall hingedly attached to one wall of the packaging pocket component and for covering the packaging pocket component (and an opening into the pocket component), and a band-fastener attached to the packaging flap wall outermost edge. Such band-fastener allows for the repeated opening and secure-closing of the flap about the packaging, without loss of closure ability over time. By "secure" is meant that upon closing of the flap and placement of the band-fastener about the closed end of the packaging, the flap will not easily reopen (i.e. not separate from the packaging closed end), absent application of a force that pushes the band-fastener off of the closed end of the packaging. Such closure relies not on adhesive, but instead on the ability of the band-fastener to encircle the closed end of the packaging, and to be restrained from sliding off of the packaging by either (a) the thickness of the packaging contents swelling the walls of the packaging closed end under the band-fastener, and/or (b) the friction between the walls of the packaging closed end (i.e. the back wall) and the band-fastener, flap-facing edge itself. By including an elastic band-fastener that is attached at least at two points to the outermost edge of the flap wall, a fastening mechanism is included which also may provide for adjustable closure of the packaging as successive articles are removed from the packaging. For example, such band-fastener may be slid up further along the back wall of the packaging towards a flap wall and pocket component seam, depending on the number of articles contained in the packaging, or may rely on the elastic properties of the band-fastener itself to maintain continuous compression on the packaging closed end, even as articles are successively removed from the packaging (and the expanded thickness is reduced). Such band-fastener allows for repeated fastening and closure of the packaging via the flap, and without the risk of adhesive degradation over time, or the cost of expensive fastening/closure mechanisms, since in one embodiment, the band-fastener is integrally formed from the packaging flap wall material itself. The specific material of the band-fastener may be selected so as to increase the elasticity and/or coefficient of friction between the band-fastener and the packaging closed end (i.e. back wall) thereby ensuring that the packaging flap remains securely in place over the pocket component. Alternatively, the band-fastener material may be selected to allow the structure to maintain a constant compressive force on the packaging closed end, either by an elastic component or by a bendable, but rigid component.

Reference now will be made in detail to various embodiments of the invention, one or more examples of which are described below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures.

Figure 1A:
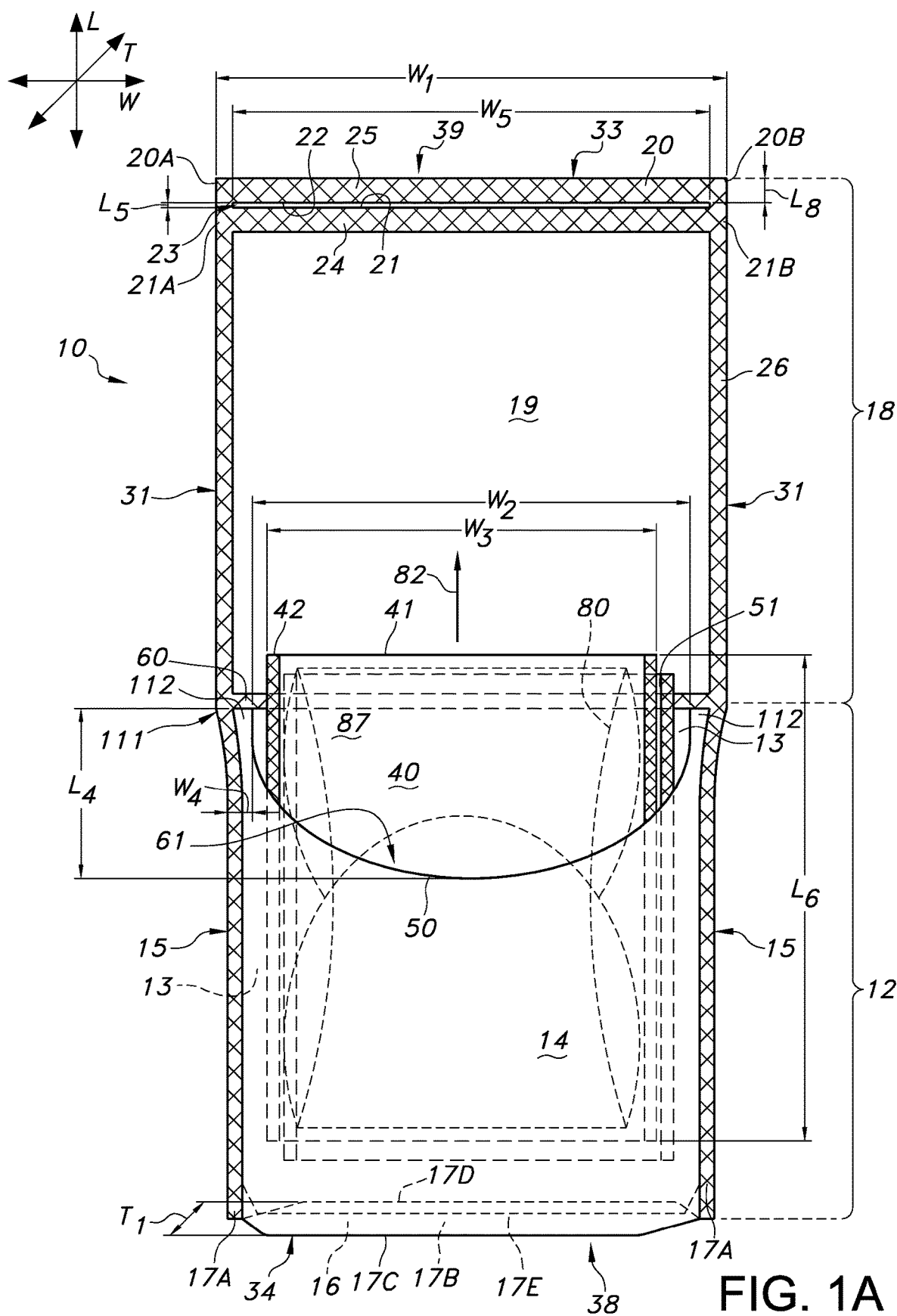
FIG. 1A illustrates a front (and opened) perspective view of a reclosable, band-fastened convenience packaging for storing a few personal care absorbent articles, and actually containing a few, individually-wrapped absorbent articles.

The invention is directed to a band-fastened packaging 10 for storing absorbent articles 80, and desirably individually-wrapped, folded absorbent articles 40, 51, as seen in the front, and opened perspective view of FIG. 1A. The band-fastened packaging 10 includes a pocket component 12 formed from at least a back wall 13 and a front wall 14. An opening 61 to the pocket component 12 is formed either between edges of the front and back walls 13, 14, or entirely within the front wall 14, through which individually-wrapped absorbent articles 40, 51 may be withdrawn from storage in the packaging 10. A packaging flap 18 (consisting primarily of a flap wall 19) is either an integral extension of, or is a non-integral structure connected to, the back wall 13. The flap wall 19 includes an outermost flap wall edge 21 (which is an uppermost flap wall edge). A band-fastener 20 is attached to this outermost edge 21 of the flap wall 19, at least at two points on the lateral-most end regions 20A, 20B of the band-fastener 20. The outermost flap wall edge 21 (also referenced herein as the flap wall outermost edge) is the uppermost edge of the flap wall 19 (as opposed to the packaging flap side edges 31).

Figure 1B:
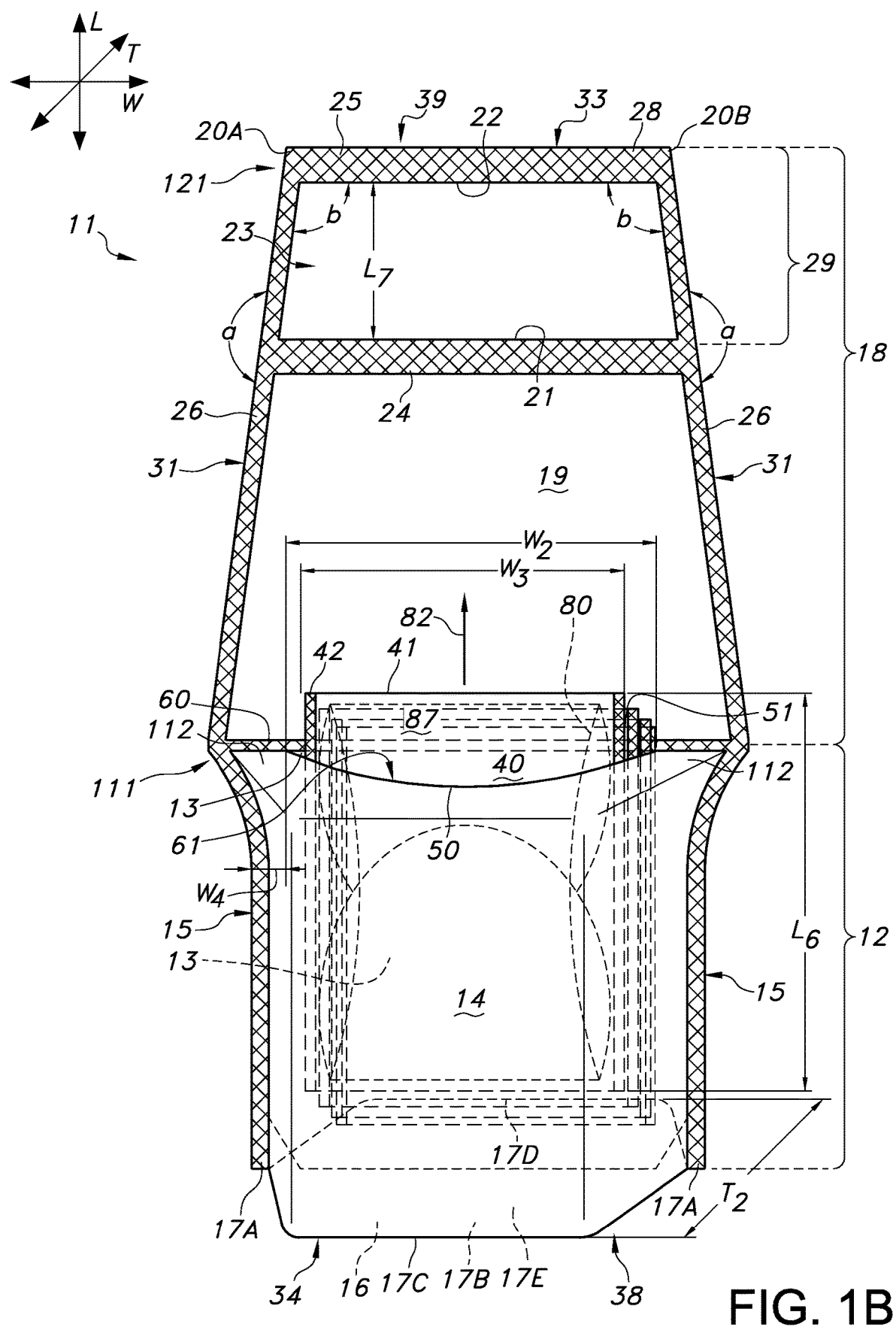
FIG. 1B illustrates a front (and opened) perspective view of an alternative embodiment of a reclosable, band-fastened convenience packaging for storing multiple personal care absorbent articles, and actually containing multiple, individually-wrapped absorbent articles.
Figure 4A:
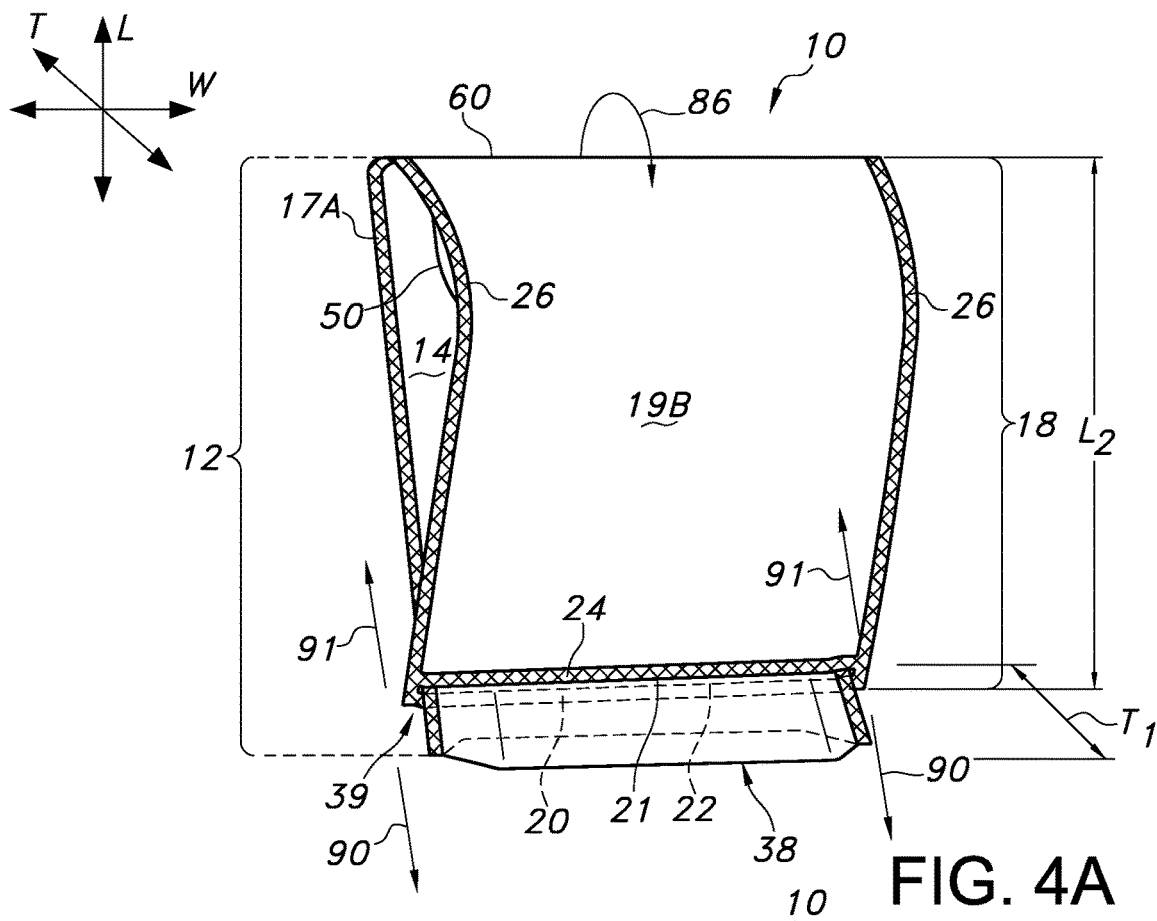
FIG. 4A illustrates a front (and closed) perspective view of the embodiment of FIGS. 1A, 1C, and 2A, showing the placement of an integrally-formed, band-fastener about the closed end of the packaging.
Figure 4B:
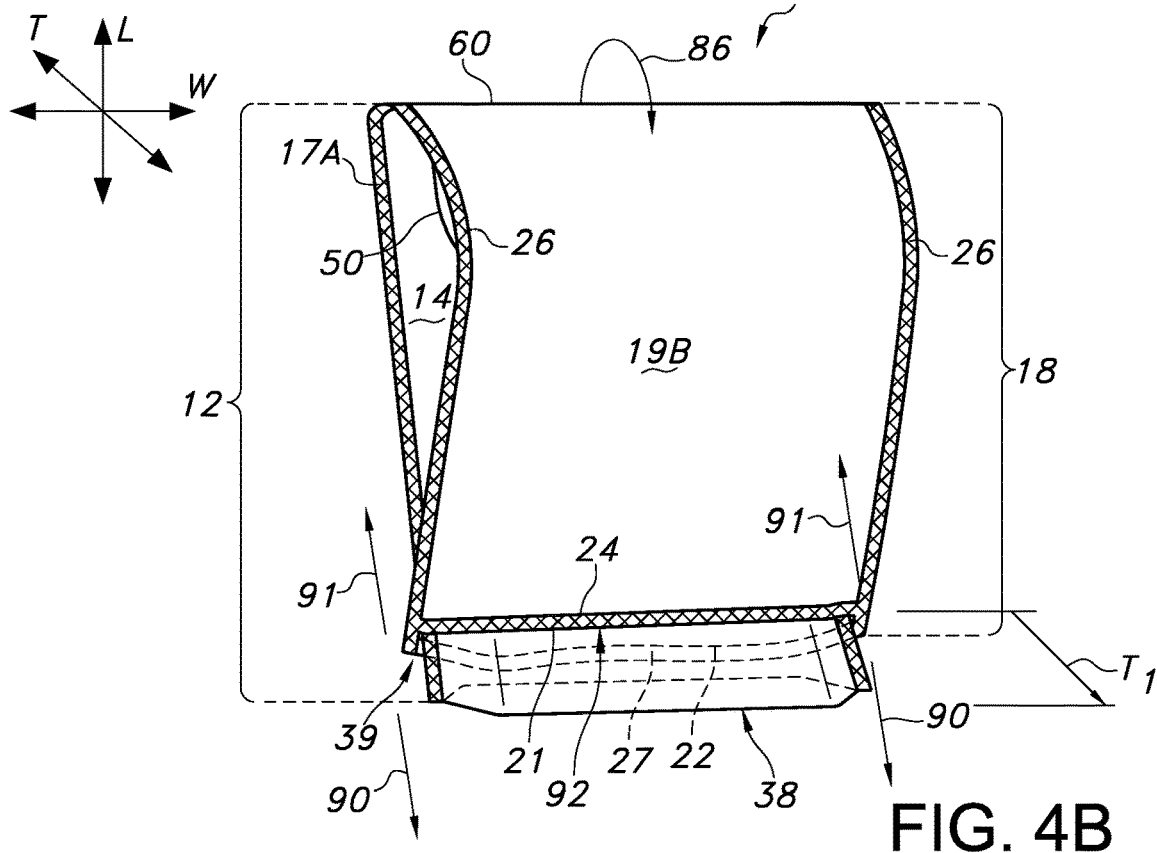
FIG. 4B illustrates a front (and closed) perspective view of the embodiment of FIG. 2C, showing the placement of an elastic band-fastener about the closed end of the packaging.
Figure 4C:
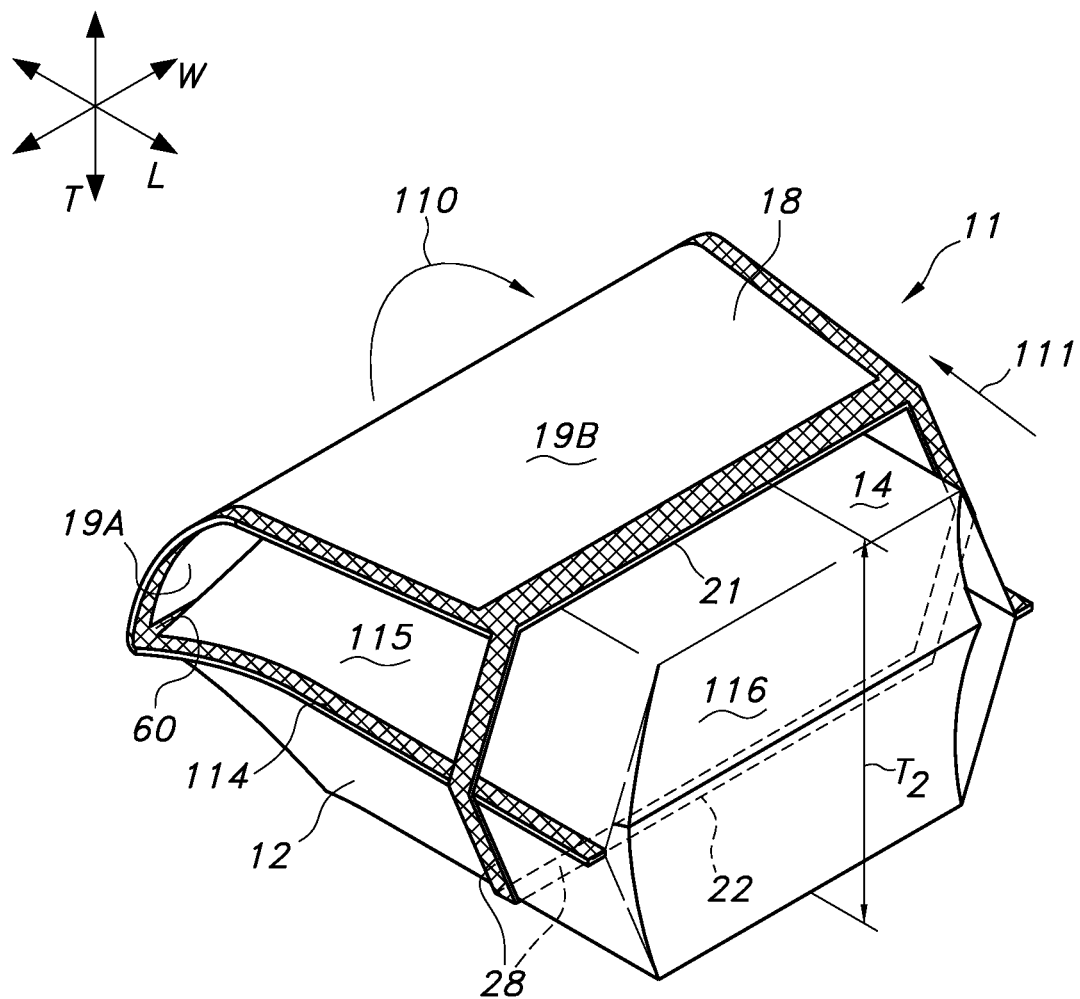
FIG. 4C illustrates a perspective view (from the bottom edge) of the embodiment of FIGS. 1B and 2D, showing the placement of the extended-length, band-fastener about the closed end of the packaging.

The band-fastened packaging 10 is portable given its overall size, and provides convenience and discreteness in the transport of such articles, which articles might normally create emotional distress for a consumer if such articles were to be seen by passersby. The packaging 10 of FIG. 1A is shown in a front perspective view and in a fully extended and generally flattened condition, with a few packaging contents (individually-wrapped absorbent articles 40, 51) visible (in both solid and phantom lines). Such packaging 10 is desirably portable, in that its length L, width W, and thickness T dimensions allow for it to easily fit within a consumer's relatively small carrying bag, purse or even, pocket. For example, it is desirable in one embodiment, for the length L1 of the overall opened, and generally flattened packaging L1 (without containing article contents such as seen in FIG. 3) to be between about 70 and 300 mm, alternatively, between about 120 and 200 mm. It is desirable in one embodiment for the length of the closed packaging L2 (as seen generally in FIG. 4A but desirably measured in a generally flattened condition without containing article contents), to be between about 35 and 100 mm, alternatively, between about 60 and 100 mm. It is desirable in one embodiment for the width W1 of the packaging (in either opened or closed condition, and desirably in a generally flattened condition without containing article contents) as seen in FIGS. 1A, 3 to be between about 25 and 120 mm, alternatively between about 50 and 90 mm. In one embodiment, the width W1 of the packaging is constant along its length (as seen for example in FIG. 3). Alternatively, the width W1 may vary along its length L1 (as seen for example in FIGS. 1A, 1B) for either aesthetic or functional purposes. For example, it may be desirable in one embodiment to have a wider packaging portion 111 adjacent the pocket component opening 61 and base of the packaging flap 18 (adjacent seam 60), as seen in FIG. 1B, so as to facilitate removal of individually-wrapped absorbent articles 40, 51 through the pocket opening 61. It may also be desirable in one embodiment, for the width W1 to be larger in the area of 121 of the packaging flap (but not actually shown as wider in FIG. 1B), in and around the location of the band-fastener 20, so as to facilitate easier use of the band-fastener 20 (as will later be described). It is desirable in one embodiment that the thickness T1, T2 of the expanded and closed packaging (including the normal full capacity of article contents) as seen in FIGS. 4A-4C, to be between about 5 and 60 mm, alternatively, between about 15 and 45 mm.

The band-fastened packaging 10 is designed to hold a relatively small number of absorbent articles 80 (such as folded absorbent articles) for ease of transporting and dispensing the articles by a consumer. If the convenience packaging 10 holds individually-wrapped absorbent articles 40, 51 (shown in partial phantom lines), rather than merely folded absorbent articles 80 (shown in phantom lines), then the reclosable, band-fastened convenience packaging 10 serves as an outer packaging for storing the inner packages containing the folded absorbent articles 80 (shown as panty liners in the disclosure). Such configuration is illustrated in FIG. 1A. The illustrated embodiment of FIG. 1A shows such packaging 10 in an opened configuration, with the packaging flap 18 in a fully extended condition, so as to allow complete access to the individually-wrapped absorbent articles 40, 51 contained therein.

The pocket component 12 which is formed at least from the back wall 13 and front wall 14, has longitudinally directed side edges 15, and an end edge 16. Such edges 15, 16 may each be sealed (i.e. bonded) or folded, although the longitudinally directed side edges 15 are illustrated in FIG. 1A as having opposing seal lines 17A along their lengths. Such seal lines 17A may be accomplished by traditional bonding techniques such as for example by ultrasonic, adhesive, or thermal bonding, or a combination thereof as are generally known in the bonding art. In one alternative embodiment, ultrasonically-bonded seal lines are employed. Alternatively, such bonding may be accomplished by needling/stitching or stapling along the opposing longitudinally directed side edges 15. As noted, such pocket component 12 includes a third edge, which functions as the end edge 16, and which may also be either sealed or folded. As illustrated in FIG. 1A, it is shown as being a folded-over edge 17B. The folded-over edge 17B and lower portions of the longitudinally directed side edges 15 of the front and back walls adjacent (and perpendicular to) the folded over edge 17B, form the packaging closed end 38.

The pocket component 12 edges 15, 16 may be formed by the mere attachment of the front 14 and back 13 walls at their peripheral edges (as shown with respect to edges 15), or alternatively, such edges may be formed from separate side and/or bottom walls that connect front and back walls together (not shown). In FIG. 1A, the bottom of the packaging 10 (packaging closed end 38) includes a distinct portion of material which was folded over, and which may optionally include a gusset-like, folded structure 17E defined by creases on the front and back walls. The folded structure is defined by creases 17C and 17D for instance in FIG. 1A. The packaging closed end 38 has an expanded thickness T1 that generally extends between one crease 17C to the other 17D. The expanded thickness T1 would be the thickness of the packaging closed end 38 when the packaging has reached its normally full capacity of absorbent articles (and in one embodiment, including the folded-over packaging flap 18 which desirably adds a de minimis amount to the expanded thickness). When the packaging 10 is emptied of contents, the closed end 38 may take on a more flattened appearance. A further example of a packaging in accordance with the invention that includes multiple side walls and a bottom wall, in addition to a front and back wall, can be seen in FIG. 4C, as will be further described below.

As illustrated in FIG. 1A, the pocket component 12 is formed from two walls 13, 14, which actually consist in one embodiment, of one sheet that has been folded over itself to form both walls 13, 14, and which walls are sealed along their longitudinally-directed side edges 15. Such folded sheet includes excess material to create the folded over edge 17E (and gusset) in one embodiment.

Each of the front 14 and back 13 walls of the various embodiments may themselves be formed from one or more sheets of material, such as a laminate of nonwoven and film sheet materials, with more sheets providing potentially more strength/durability to the packaging 10. Such laminate construction may also provide different textural surfaces to the overall packaging 10, such as a more textile-like feel (from nonwoven sheeting) along the exterior surface of the packaging 10 and a smooth feel (from film sheeting) along the inside surface of the pocket component 12. Such smooth surface may also enhance the ability of the individually-wrapped absorbent articles 40, 51 within the packaging 10 to slide more easily from the pocket component 12 when needed.

At least an exposed opening edge 50 of the front wall 14, or in some instances, exposed edges of both of the walls 13, 14 of the pocket component 12 define an opening 61 into the pocket component 12. For example, the opening 61 into the pocket (the pocket being the space between the at least two walls, and in one embodiment, between multiple walls) may be either placed solely in the front wall 14 (as seen in FIG. 3), or between the front 14 wall upper exposed edge 50 and the back wall 13 (as seen in FIG. 1A). The opening 61 into the pocket component 12 may be between and through two generally aligned straight-edged, front and back wall edges (not shown), or alternatively, between two walls that have dissimilar lengths along their widths W (as seen in FIG. 1A). For example, in the embodiment of FIG. 1A, the front wall 14 defines an exposed opening edge 50 that includes in one embodiment, a half-moon shaped portion, in order to allow for easy viewing and grasping of individually-wrapped absorbent articles 40, 51 from the interior space of the pocket component 12. In FIG. 1A, the pocket component 12 is formed from a front wall 14 having varied lengths along its width (creating the half-moon shaped opening edge portion) and a longer length back wall 13. Also in the illustrated embodiment, the back wall 13 extends (in length) beyond the pocket component 12 to become the flap wall 19 of the packaging flap 18. The flap wall 19 of the packaging flap 18 may be integral with the back wall 13. However, since in one embodiment the back wall 13 may be formed from a separate, non-integral material than the packaging flap 18, the flap wall 19 making up the majority of the packaging flap 18 will be referenced by its own number 19, as opposed to 13 for ease of understanding.

By including an exposed opening edge 50 having a portion (such as the half-moon shaped portion) that is narrower in width W2 than the overall width W1 of the packaging 10, the absorbent articles may fit more tightly within the packaging 10, especially if the width W3 of the absorbent articles or individually-wrapped absorbent articles 40, 51 is larger than that W2 of the exposed opening edge 50 (not shown). In such an embodiment, it may be desirable to design wrappers for individually-wrapped absorbent articles 40, 51 that more easily slide past the exposed opening edge 50 or have lower coefficients of friction with respect to the inside surfaces of the pocket component 12.

Lateral portions 112 of the front wall 14 adjacent to the exposed opening edge 50 (adjacent the half-moon shaped portion for example), may in one embodiment be bonded to the back wall 13 such that the front and back walls are bonded together not only along the longitudinally directed side edges 15, but also at the lateral portions 112. Such lateral portions 112 of the front wall 14 may be bonded to the back wall 13 along seam/bond line 60, or along an area adjacent seam line 60.

As noted, in the illustrated packaging 10 of FIG. 1A, the back wall 13 forms the back surface of the pocket component 12 and may extend longer than the front wall 14, thereby forming also the flap wall 19. The flap wall 19 of the packaging flap 18 may be a mere integral extension of the back wall 13, or alternatively, a separately-formed extension that is attached to the back wall 13. The flap wall 19 may therefore be fashioned from the same material or a different material than the back wall 13.

While shown in FIG. 1A as including a half-moon shaped portion, the exposed opening edge 50 may alternatively be of a variety of shapes, such as a straight line, a triangular shape, a semi-circular, semi-oval, or abstract curvilinear shape. The front wall 14 defines the opening edge 50 which may extend (as shown) laterally beyond longitudinally-directed side edges of individually-wrapped absorbent articles 40, 51. In one embodiment, the front wall 14 may extend to and be bonded to the back wall 13 along portions of a seam 60. Along this seam 60, the flap wall 19 of the packaging flap 18 is also connected to the back wall 13, if of non-integral construction. Even if of an integral construction, such seam 60 may be present so as to provide a hinge or fold-line for the packaging flap 18.

In an alternative embodiment, the front wall 14 may completely define the opening 61 on all sides (as seen for example in the alternative embodiment of FIG. 3, in which a semi-oval exposed opening edge 50 is placed only in the front wall 14). In such an embodiment, the absorbent articles or individually-wrapped absorbent articles 40, 51 would fit even more tightly within the packaging 10. In one embodiment, the width W4 of the relatively narrow lateral pieces of front wall 14 that help define the opening 61 and are adjacent to the curved, opening edge portion, are each between about 0.1 and 30 mm in width. In one embodiment, the width W2 of the opening 61 defined by the exposed opening edge 50 or a portion thereof, is between about 25 and 120 mm, and the length L4 (on FIG. 1A) is between about 0 and 90 mm, alternatively, between about 1 and 90 mm, alternatively between about 20 and 40 mm. It should be appreciated that the length L4 of the opening edge 50 is distinguished from the depth or length L2 of the pocket component. If the length L4 is 0 mm, then the opening will be formed having at least one straight (level) opening edge across the packaging width.

As noted, the front and back walls 14, 13 may meet and be bonded together in one embodiment, at least partially along seam 60, which seam 60 also forms the fold line (or hinge) in the packaging 10, about which the packaging flap 18 folds. The packaging flap 18 is therefore hingedly connected to the back wall 13. In an alternative embodiment, the opening edge 50 may be level with and aligned with the seam 60 level (not shown), such that there is no recessed exposed edge portion along the front wall 14 as would be provided by the half-moon shaped, exposed edge portion. In still a further alternative embodiment, the front wall 14 may include an exposed opening edge 50 that is aligned with the level of the seam 60 but which is not bonded to the back wall 13, except along the front and back wall longitudinal directed side edges 15. In such an embodiment, a non-curved opening edge would extend to almost the full width dimension of the packaging 10, rather than to a width that is significantly shorter than the packaging width (as with the half-moon shaped exposed edge portion shown in FIG. 1A). Such embodiment would provide for the widest possible opening 61 in the packaging 10 pocket component 12.

The seam 60 (at the intersection of the base of the packaging flap 18 and the upper edge of the pocket component 12, back wall 13), forms the fold line about which the packaging flap 18 can be folded in order to close/cover the opening 61 of the pocket component 12, and bring the packaging flap 18 to sit immediately adjacent the front wall 14. The flap wall 19 of the packaging flap 18 forms the protective barrier between the external environment of the packaging 10, and the individually-wrapped absorbent articles 40, 51 contained in the packaging 10. As with the front and back walls 14, 13 (which create the pocket component 12), the flap wall 19 may itself also be formed from multiple sheets (such as laminated sheets) to provide additional strength and durability over the life of the packaging 10, and also to provide a difference in texture between the packaging outer surface and inner surface. The flap wall 19 in particular, has an interior-facing surface 19A and an exterior facing surface 19B (as seen in FIG. 3). The exterior-facing surface 19B may be formed in one embodiment, from a nonwoven sheet in order to provide a textile-like feel to the exterior-facing surface 19B. Desirably in one embodiment, the flap wall 19 includes peripheral edge seal lines 24, 26 which extend at least partially around the flap wall 19, and at least some of which 26 are aligned (along the longitudinally directed flap side edges 31) with the opposing edge seal lines 17A of the front 14 and back 13 walls that form the pocket component 12. The edge seal lines all provide in one embodiment, a certain relative rigidity to the pocket component 12 and flap wall 19 outermost/peripheral edges (compared to more centrally located pocket and flap wall regions). The flap wall 19 of the packaging flap 18 ends in the outermost flap wall edge 21, which outermost flap wall edge 21 desirably includes an edge seal line 24 as noted. Therefore in one embodiment, seal lines extend either continuously or discontinuously along the peripheral edges of each planar surface of the packaging 10. While not shown in FIG. 1A, such a seal line may also be placed along the opening edge 50 to provide additional strength and rigidity to this exposed edge.

As seen in FIG. 1A, the reclosable, band-fastened convenience packaging 10 also includes a band-fastener 20 which is attached at two lateral-most end regions 20A, 20B to the outermost flap wall edge 21 of the flap wall 19. The band-fastener 20 is attached at least at two points at the lateral-most end regions 20A, 20B. The two attachment points are in one embodiment, separated by a continuous spatial gap or opening 23. The spatial gap 23 may be of uniform length L5 across its width (FIG. 1A), or of nonuniform length (FIGS. 1B, 2C). The spatial gap 23 may also be of nonuniform width depending on where it is measured along its length (FIG. 1B). In an alternative embodiment, as will be described below, the band-fastener 20 may be attached via a frangible seam 57 to more than two points of the flap wall, along the outermost flap wall edge 21. In such an alternative embodiment, the action of breaking the frangible seam 57 by a consumer creates the spatial gap 23. The band-fastener 20 may be attached to the outermost flap wall edge 21 at the outermost flap wall edge, lateral most regions 21A, 21B, or at locations inward from the outermost flap wall edge, lateral most regions.

Figure 1C:
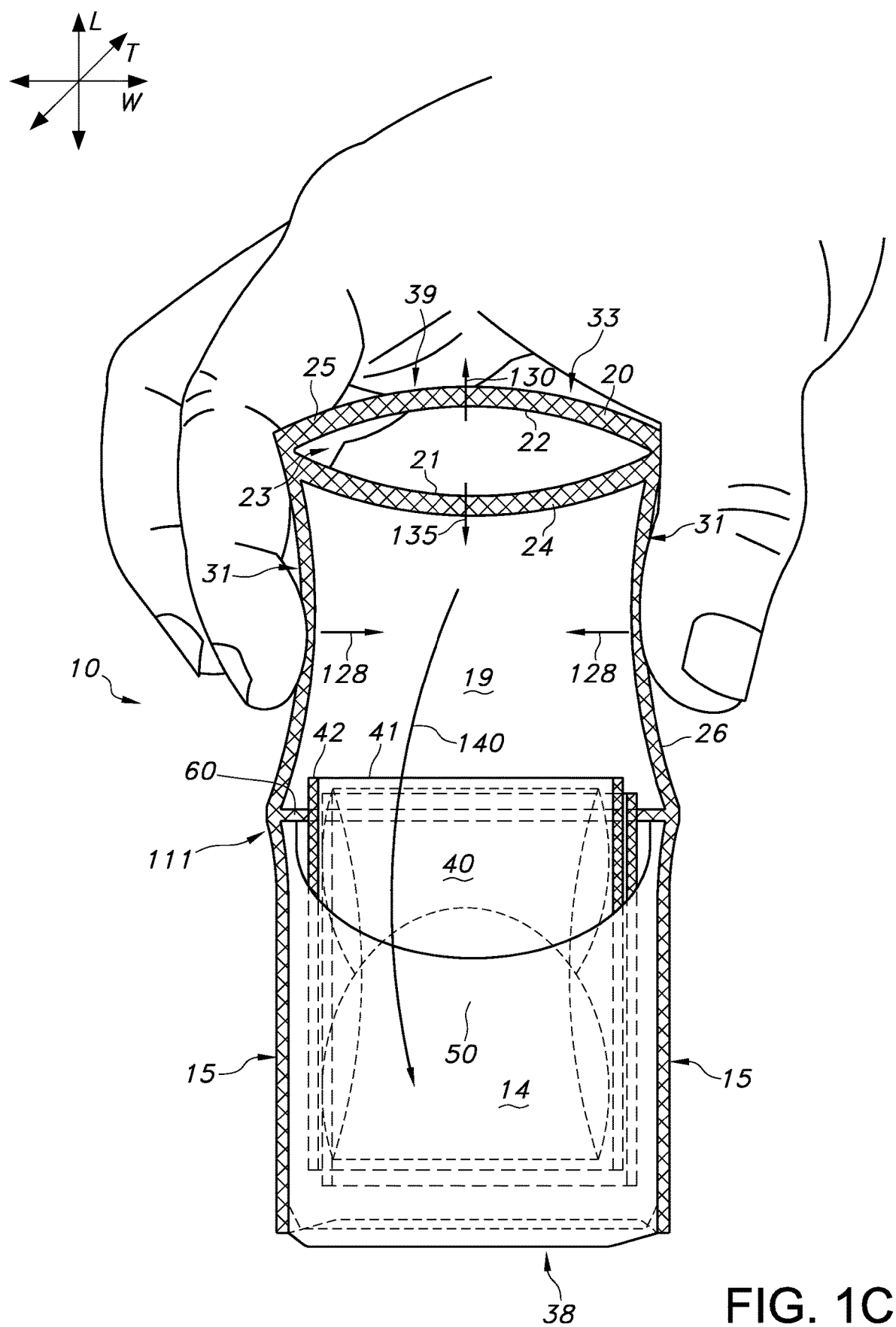
FIG. 1C illustrates a front (and opened) perspective view of the reclosable, band-fastened convenience packaging of FIG. 1A in partial operation, as a consumer is preparing to close the packaging.

The spatial gap 23 has an "at rest" configuration and an "altered" configuration. For the purpose of this disclosure, the term "at rest" shall mean that configuration of a packaging feature, such as the band-fastener 27 or the spatial gap 23, that is present when the packaging flap 18 is in its original, fully extended and opened orientation (such as seen in FIG. 3). The term "altered" configuration shall refer to a configuration in which the feature, such as the band-fastener 27 or spatial gap 23 is either being compressed or extended as a result of a consumer action (such as seen in FIG. 1C), or when the band-fastener 27 or spatial gap 23 is being extended as a result of a band-fastener 20, 27 being placed and held about the packaging closed end 38. Desirably, in one embodiment, the "at rest" spatial gap 23 extends continuously between at least two attachment points a distance (W5) of between about 2 and 115 mm, alternatively, between about 2 and 100 mm, alternatively, between about 2 and 30 mm. It should be appreciated that depending on packaging configuration, the altered spatial gap and band-fastener dimensions may change as a result of articles being either removed from or restocked in the packaging.

The band-fastener 20 is situated at the packaging, extended flap end 39, when the packaging 10 is laid in a fully extended, flat, and open configuration. The outermost flap wall edge 21 is adjacent the band-fastener 20 flap-facing inner edge 22.

In the embodiment of FIG. 1A, a relatively short spatial gap 23 defined by L5, is present between the outermost flap wall edge 21 and the flap-facing inner edge 22 of the band-fastener 20. The spatial gap 23 may be of minimal length L5 between the outermost flap wall edge 21 and the flap-facing inner edge 22 of the band-fastener 20. For example, in one embodiment, the minimal length may be in an amount between about 0 to 50 mm, alternatively, between about 0 to 30 mm, alternatively between about an amount larger than 0 mm to 30 mm, alternatively between about 1 to 10 mm. Still in a further embodiment, the minimal length may be between about 1 to 3 mm. The spatial gap 23 of FIG. 1A extends in one embodiment continuously between the two attachment points of the band-fastener 20 adjacent the packaging flap longitudinally directed side edges 31. In the embodiment illustrated in FIG. 1A, the band-fastener 20 is of integral construction with the flap wall 19, and also includes a seal line along its edge 25, for extra strength and rigidity along the full width of the band-fastener 20 structure. In this case, the entirety of the band-fastener 20 is encompassed by the seal line 25, but need not be. The band-fastener 20 also includes a band-fastener, outermost edge 33 that faces away from the band-fastener, flap-facing inner edge 22. The band-fastener, outermost edge 33 also forms the outermost edge of the packaging flap 18 overall structure.

The packaging flap 18 may itself be of a wide variety of shapes, such as rectangular, square, curvilinear, tapering (as seen in FIG. 1B), or abstract. The seal lines on the packaging may be continuous (as shown) or discontinuous (not shown) about the peripheral edges of the packaging, and may vary in width depending on location on the packaging 10. For example, in some locations greater rigidity may be desired. In such situations, a wider seal line may be preferred. Further, some locations within the packaging, such as adjacent the packaging exposed opening edges, may encounter greater stress as a result of the flap opening and closing and article removal, and therefore would benefit from a wider seal line. The spatial gap 23 formed between the flap wall outermost edge 21 and the flap-facing inner edge 22 of the band-fastener may be of a variety of shapes (such as trapezoidal, rectangular, square, and oval) so as to better accommodate insertion of the packaging closed end 38. Further, such spatial gap 23, or rather the outermost flap wall edge 21 may be curved (such as with the widest portion of the curve opening facing the packaging closed end 38) so as to better accommodate insertion of the packaging closed end 38, during packaging closure.

In the embodiment shown in FIG. 1A, the band-fastener 20 is desirably pliable, in that it may be easily placed about the packaging closed end 38, once the packaging flap 18 is folded about the seam 60 and placed adjacent to the front wall 14. This closure operation will be further described below, but is illustrated in detail in FIG. 4A. Essentially, by being "pliable", is meant that the outermost flap wall edge 21 between the two attachment points (of regions 20A, 20B), may be moved apart from the band-fastener, flap-facing inner edge 22.

Desirably, in one embodiment, the length or depth of the pocket component L2 (as seen on FIG. 3) is between about 20 and 150 mm, alternatively, between about 60 and 100 mm, while the length L3 of the packaging flap 18 (as seen in FIG. 3) is between about 20 and 150 mm, alternatively, between about 60 and 100 mm, when both are in a fully extended, generally flattened condition (and without contents). These lengths occur while the packaging 10 is in a fully opened state as seen in FIG. 3. The lengths L2 and L3 need not necessarily be equal, but are in one embodiment, equal. In an alternative, such packaging flap 18 is of a shorter length L3 than the pocket component 12 length L2. Also, in the embodiment illustrated in FIG. 1A, the band-fastener 20 seal line 25 is of similar construction as the packaging 10 seal lines 24, 26, 17A. If fact, it may be formed of the same sealed material or processes as all of the adjacent seal lines/sealed edges.

The illustrated packaging 10 of FIG. 1A, includes within its pocket component 12, a few individually-wrapped absorbent articles 40, 51 in the form of folded feminine-care panty liners 80 contained in wrappers 87. As will later be described, the individually-wrapped absorbent articles 40, 51 themselves have sealed edges 42 and perpendicularly adjacent folded edges 41 on the individual wrappers 87. The wrappers 87 are desirably positioned within the pocket component 12 such that the wrapper sealed edges 42 are adjacent the opening edge (e.g. the half-moon shaped portion of the exposed opening edge 50) such that the individually-wrapped absorbent articles 40, 51 may more easily be slid out from the pocket component 12 in accordance with directional arrow 82.

A front perspective view of an alternative embodiment of an open but reclosable, band-fastened packaging 10 is illustrated in FIG. 1B. As seen in such figure, the width of the packaging 10 varies along the length of the opened packaging 10, such that a wider area 111 is present near the base of the packaging flap 18 and adjacent the upper edge of the pocket component 12. That is, the back wall 13 and flap wall 19 include in this alternative embodiment, wider areas along their lengths. Such wider areas ensure that the packaging flap 18 completely covers the opening into the pocket component 12, once the packaging flap 18 is folded about the seam 60. The alternative embodiment of the packaging 11 in FIG. 1B allows for the storage of larger numbers of individually-wrapped absorbent articles 40, 51 than the embodiment of FIG. 1A, given that its expanded thickness T2 is relatively larger than that of the embodiment of FIG. 1A. The band-fastener 28 in FIG. 1B is also of an extended length, having extended-length side edges 29 in order to allow for the encircling of the relatively larger expanded thickness of the packaging closed end 38 (described further below).

In order to partially demonstrate the closing operation that allows for the packaging flap 18 to be placed in condition to receive the packaging closed end 38 within the spatial gap 23 (opening), an illustration is provided in FIG. 1C which shows the hand of a consumer compressing the side edges 31 of the packaging flap 18 (flap wall) together. This operation can occur for multiple embodiments of the packaging 10 in which the construction material of the packaging 10 is of a flexible material. The compression of the packaging flap 18 at the locations noted and in accordance with directional arrows 128, causes the outermost flap wall edge 21 to taper downward as in accordance with directional arrow 135. The band-fastener 20 (especially if of a non-elastic, but flexible material) bends outward in accordance with directional arrow 130. The opening of the spatial gap 23 is therefore made more obvious by this movement, and upon the folding of the packaging flap 18 in accordance with directional arrow 140 about the seam 60, the packaging closed end 38 may be inserted as would a tab-like structure (in some instances following the slight compression of the packaging closed end 38) through the opening of the spatial gap 23 for closure of the packaging 10 and securement of the packaging flap 18 about the packaging 10 closed end 38.

Figure 2A:
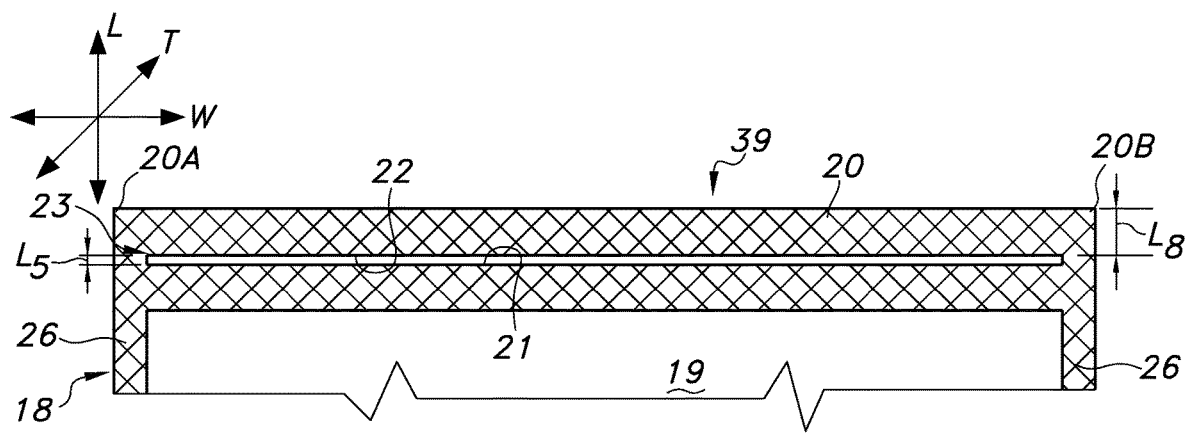
FIG. 2A illustrates a partial front (and opened) perspective view of an embodiment of a band-fastener on a packaging flap, for use on reclosable, band-fastened convenience packaging.
Figure 2B:
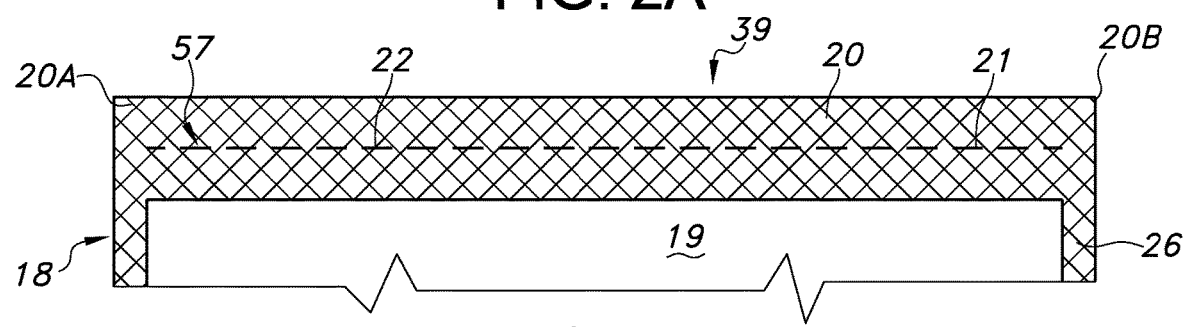
FIG. 2B illustrates a partial front (and opened) perspective view of an alternative embodiment of a band-fastener on a packaging flap, for use on reclosable, band-fastened convenience packaging.
Figure 2C:
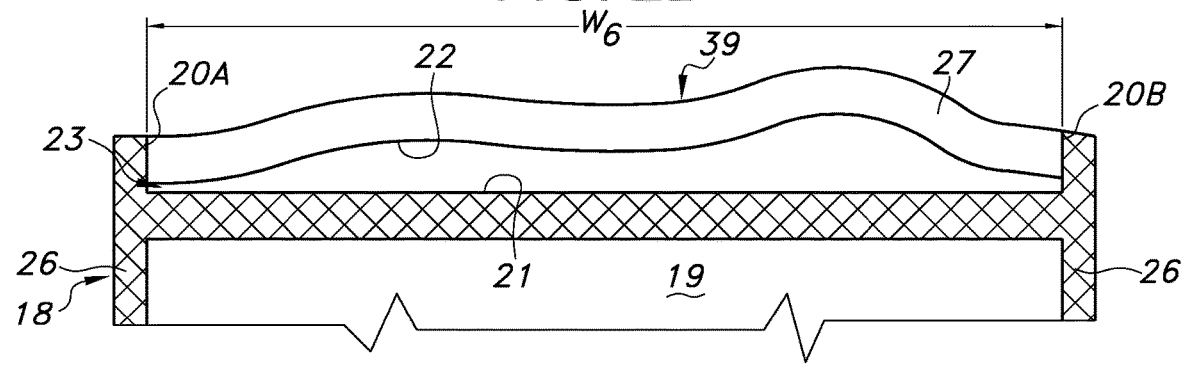
FIG. 2C illustrates a partial front (and opened) perspective view of an alternative embodiment of a band-fastener on a packaging flap, for use on reclosable, band-fastened convenience packaging.

A series of exemplary band-fastener 20, 27, 28 alternative designs for use with the packaging 10 of the invention are illustrated in the partial, but enlarged front perspective views of FIGS. 2A-2E. Some of the band-fasteners 20, 28 are illustrated as being integral with the flap wall 19, while others are nonintegral 27. For example, as seen in FIG. 2A a band-fastener 20 is shown as being present at the packaging flap end 39 such that a relatively narrow spatial gap of length L5 is present between the band-fastener, flap-facing inner edge 22 and the flap wall outermost edge 21. The spatial gap 23 is of uniform length along the width of the flap wall 19. The length L8 of the band-fastener 20 is also uniform along the width of the flap wall 19.

While the band-fastener 20 is desirably in one embodiment, integral with the flap wall 19, in other embodiments it may not be formed from the same material as that of the flap wall 19. The band-fastener 20 is desirably of a polymeric film material, such as a polyolefin. Desirably, such packaging 10, packaging flap wall 19, and band-fastener 20 are all constructed from the same material, such as for example a polymeric film material, such as a polyolefin. Desirably, such packaging, packaging flap wall, and band-fastener are all constructed from a polyolefin film, such as a polyethylene, polypropylene, polymethylpentene, polybutene-1 film, or alternatively from polyolefin elastomers, polyisobutylene, ethylene propylene rubber (EPR), ethylene propylene diene monomer (M-class) rubber (EPDM rubber) polyethylene, rayon and nylon. The film forming the packaging 10 is desirably in one embodiment, a polyethylene film having a basis weight of between about 5 and 120 grams per square meter (gsm), alternatively, between about 25 and 60 gsm.

Alternatively, such flap wall and/or band-fastener is constructed of an extensible or elastic material such as for example polyolefin, rubbers and other polymers. Such materials may specifically include extensible or elastic polyethylene, polypropylene, polymethylpentene, polybutene-1, polyolefin elastomers, polyisobutylene, ethylene propylene rubber (EPR), ethylene propylene diene monomer (M-class) rubber (EPDM rubber) polyethylene, rayon and nylon. In one alternative embodiment, such flap wall 19 and band-fastener 20, 27, 28 are each formed from flexible but nonelastic materials such as for example, a nonelastic polyolefin. It should be understood that film used in the packaging 10 may be produced using traditional film-forming processes such as extrusion, blown film, and stretching processes.

In another alternative embodiment, such packaging material (including the band-fastener 20) may be formed from tissue-based sheeting, or nonwoven sheet materials, such as for example TABCW, TBCW, spunbond, or a spunbond and meltblown nonwoven laminate. Such nonwoven packaging material may have in one embodiment a basis weight of between about 15 and 30 gsm. Alternatively, such packaging material may be formed from a nonwoven and film laminate of the materials heretofore described. Additional flexible sheet materials that may be used in accordance with the invention include metal foils and the materials that are described in European Patent 1357877B1 to Ling et al., which is hereby incorporated by reference hereto in its entirety.

In a further embodiment, the band-fastener 20 is formed of a different material than the flap wall 19, and is formed of an elastic or extensible material, so as to allow it to be at least stretched about the closed end 38 of the packaging 10, rather than merely spread open at the spatial gap 23 and placed around a compressible, packaging closed end 38. If the band-fastener 20 is elastic, it may be both stretched about a compressible, packaging closed end 38 and also allowed to retract so as to apply a continuous compression force upon the closed end 38 and further secure the packaging flap 18 about the packaging 10. This compression force would be in addition to the band-fastener 20 merely surrounding a packaging closed end 38 and securing the packaging flap 18 in place on the back wall 13 via frictional forces between the two structures.

In the alternative embodiment illustrated in FIG. 2B, rather than having the integral band-fastener 20 be formed of a material that is at least initially separated from the flap wall 19 (i.e. separated continuously along the flap width by spatial gap 23, except at the two lateral-most edge regions 20A, 20B where the at least two separated attachment points are located), it is instead formed of a material separable from the outermost edge 21 of the flap wall 19 only upon the rupturing of a frangible seam (created by a line of weakness or perforation line) 57 between the outermost flap wall edge 21 and the flap-facing inner edge 22 of the band-fastener 20. That is, at the time of initial packaging 10 use, the band-fastener 20 is almost fully integrated with the flap wall outermost edge 21, except for discrete embossments or perforations, and may be separated from the flap wall outermost edge 21 only by rupturing a line of weakness/ perforation line 57. Following the rupturing of the frangible seam 57, the band-fastener 20 remains attached to the flap wall 19 at the band-fastener 20 lateral-most end regions 20A, 20B, as was described in prior embodiments. As with the previously described embodiments, the band-fastener 20 may be formed from the same material as the flap wall 19, or of a different material, such as a more elastic or stretchable material than the flap wall 19. Alternatively, both the band-fastener 20 and the flap wall 19 of the packaging flap 18 may be formed from either an elastic or stretchable material. The line of weakness or perforation line 57 may be formed through known material aperturing or weakening processes, such as for example, by embossing, selective melting, aperturing, cutting, slitting, or puncturing processes as are generally known in the art. Such embossments or apertures may be formed in a series of aligned dashes (as shown), circles, other geometric shapes, or a combination thereof. Further, such line of weakness may be formed from a combination of embossments and apertures. As shown in the embodiment of FIG. 2B, a seal line/sealed edge may still be present along the flap outermost flap wall edge 21, and the flap-facing inner edge 22 of the band-fastener 20, despite the presence of the frangible seam (which frangible seam ends short of the lateral-most, longitudinally directed flap side edges 31). While shown as a straight line for ease of manufacturing, it should also be appreciated that the frangible seam 57 may be curved or presented in another shape.

In yet a further alternative embodiment, as shown in the partial front perspective view of FIG. 2C, the band-fastener 27 may be formed from a material different from that of the rest of the flap wall 19, and is attached to the flap wall 19 at only the band-fastener 27 lateral most end-regions 20A and 20B. Such band-fastener 27 may be for example, formed from an elastic band, such as a natural rubber, rubber-like, or polymeric band that is capable of stretching and retracting along its length. In such an embodiment, such elastic band 27 is desirably in one embodiment, initially taut enough to be placed about a packaging closed end 38 (upon folding of the packaging flap 18 about the seam 60) and to maintain a compressive force on the packaging closed end 38 in accordance with directional arrow 92 (as seen in FIG. 4B for example), but need not be stretched open until placement about the packaging closed end 38. Alternatively, the elastic band-fastener may be a taut elastic band (not shown) such that the consumer needs to extend it prior to placement about the packaging closed end 38. Alternatively, such elastic band-fastener 27 may be loose as shown, and have a nonuniform length spatial gap 23 between the flap-facing inner edge 22 of the band-fastener 27 and the outermost edge 21 of the flap wall 19. Such elastic band-fasteners 27 desirably maintain pressure on the packaging closed end 38 throughout the useful life of the packaging 10 so as to adjust the spatial gap 23 to the total number of article contents or thickness of articles within the packaging 10. That is, as individually-wrapped articles 40, 51 are removed from the packaging 10, the spatial gap (opening) 23 shrinks as a result of the elastic band-fastener 27 being less elongated. The elastic band-fastener 27 adjusts to accommodate different numbers of packaging contents (and actually increases in length with the restocking of contents in the packaging). When packaging 10 utilizes an elastic band-fastener 27, the elastic band-fastener would potentially be in a stretched configuration when the packaging 10 is securely closed (packaging end inserted into spatial gap and packaging is full to capacity with contents), and in a nonstretched configuration when the packaging 10 is opened with the packaging flap extended.

An elastic band-fastener 27 is desirable in that it can also provide a higher level of friction against the back wall 13 of the packaging 10, thereby preventing the inadvertent separation of the packaging flap 18 and the subsequent opening of the pocket component 12 to the outside environment. As shown in the embodiment of FIG. 2C, a seal line may still be present along the flap wall outermost edge 21.

Figure 2E:
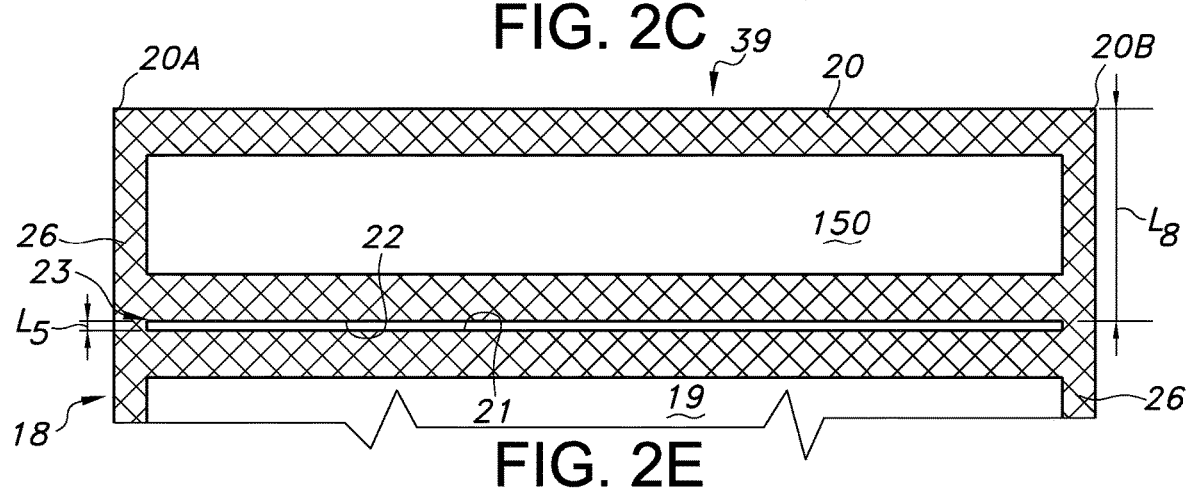
FIG. 2E illustrates a partial front (and opened) perspective view of an alternative embodiment of a band-fastener on a packaging flap, for use on a reclosable, band-fastened convenience packaging.
Figure 2D:
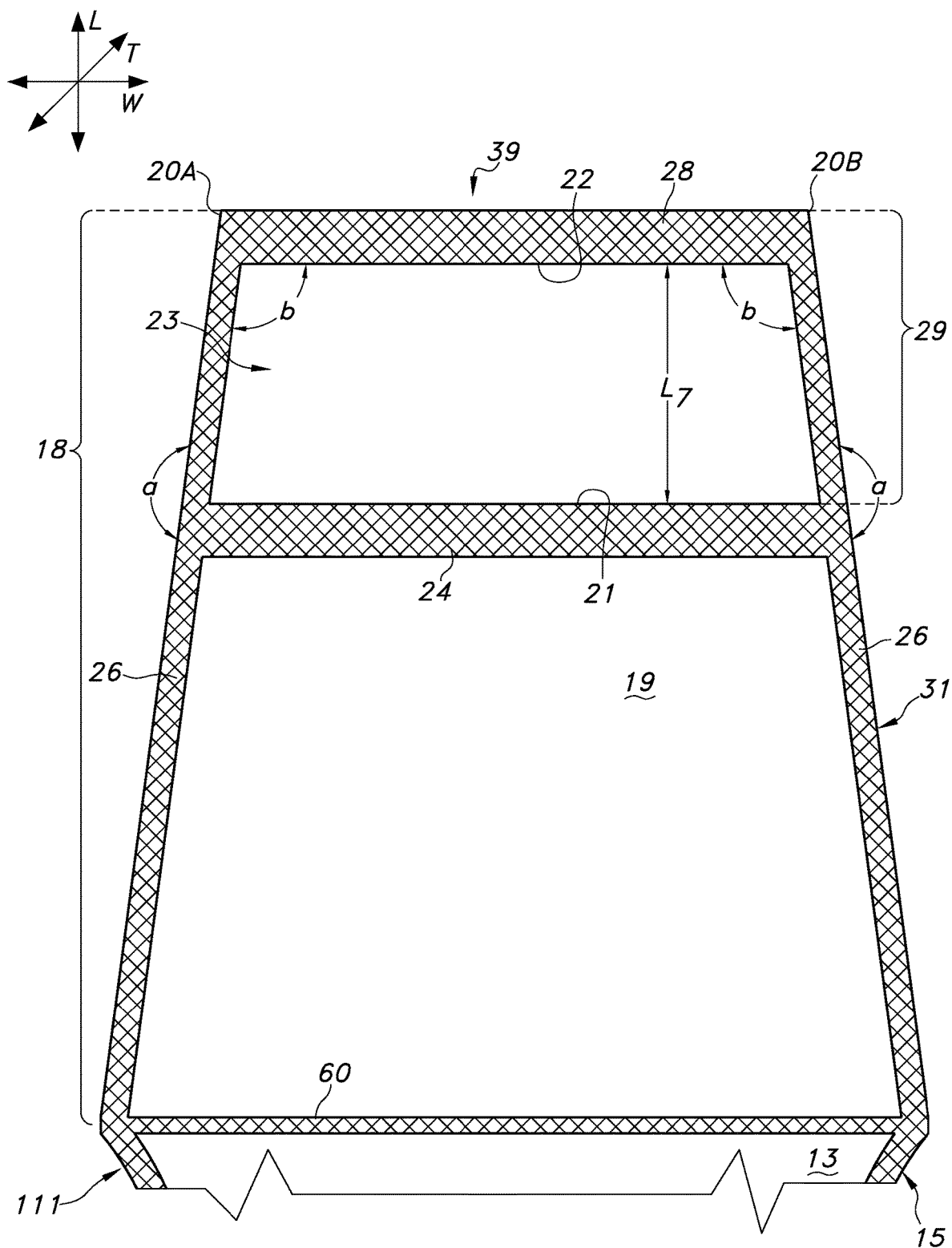
FIG. 2D illustrates a partial front (and opened) perspective view of an alternative embodiment of a band-fastener on a packaging flap, for use on a reclosable, band-fastened convenience packaging.

In still yet another alternative embodiment, the band-fastener 28 may be an extended-length band-fastener, as seen in the partial front perspective view of FIGS. 2D, 4C. The extended-length band-fastener 28 may be physically separated from the flap wall outermost edge 21 by a relatively larger spatial gap 23 defined by length L7. Such gap 23 may be in one embodiment, between about 10 and 70 mm, alternatively, between about 20 and 40 mm. By including a larger spatial gap 23 between the band-fastener, flap-facing inner edge 22 and the flap wall 19 outermost edge 21, the packaging 10 may be able to accommodate a larger number of absorbent articles, or individually-wrapped absorbent articles 40, 51, or larger articles, as the larger gap 23 adjacent the band-fastener 28 allows for the band-fastener 28 to surround a thicker packaging closed end 38, without rupturing of the band-fastener (and without the need for use of elastic or extensible construction materials as the basis of the band-fastener 28). Such benefit may also be provided with an appropriately selected elastic band-fastener as previously described. The extended-length band-fastener 28 of FIG. 2D also provides, through its extended length side edges 29, the additional benefit of serving as a packaging 10 carrying handle, when the packaging 10 is in an open, fully extended configuration. In FIGS. 1B (and 2D), the extended-length band-fastener 28 includes in one embodiment, extended-length side edges 29, at an angle>a with respect to the flap wall 19 longitudinally-directed side edge 31. While such angle appears in one embodiment to be approximately 180 degrees, desirably in one embodiment>a is between about 150 and 210 degrees, alternatively, between about 165 and 195 degrees. Additionally, it is desirable in one embodiment of the extended-length band-fastener 28 to include two interiorly situated, relatively large angles "b", at the juncture of the extended-length side edges 29 and the flap-facing inner edge 22. Such angles "b" may be in one embodiment approximately 90 degrees, alternatively between about 60 and 120 degrees, alternatively between about 80 and 100 degrees. In still a further alternative embodiment, such interior band-fastener edges (between the extended-length band fastener 28 and the extended-length side edges 29) have rounded profiles (not shown) in place of the more squared profiles shown in the figures. As shown, a seal line/sealed edge may still be present along the outermost flap wall edge 21, the extended-length side edges 29, and the extended-length, band-fastener 28 so as to provide some level of rigidity and strength to the overall structure.

The at rest, band-fastener width W6 (such as seen in FIG. 2C) may be varied according to design preferences and band-fastener material construction. For example, it may be desirable to have the at-rest, band-fastener width be equal to the width W1 of the packaging 10. Desirably, in one embodiment, the band-fastener width W6 is between 85% to 115% of the width W1 of the packaging. In an alternative, it can be 105% of the width of W1. For elastic or extensible band-fasteners, the width W6 may be less than that of the packaging W1. For extended-length band-fasteners, the width may be longer than the width W1 of the packaging 10. For rigid but bendable band-fasteners as described further below, the at-rest width may be larger than the packaging width.

In yet a further alternative embodiment as illustrated in FIG. 2E, a band-fastener 20 is provided on a packaging, in which the spatial gap 23 between the outermost flap wall edge 21 and the band-fastener, flap-facing inner edge 22 is set apart a relatively greater distance from the band-fastener outermost edge 33 than in previously described embodiments. In such embodiment, the band-fastener 20 includes a plane of sheet material 150 between edges 22 and 39, such that the distance L8 is relatively larger along the width of the band-fastener. In such embodiment, by including a spatial gap 23 relatively closer to the pocket component 12 (and seam 60, if present), the flap may be more likely to stay in a closed position and be less likely to inadvertently disengage, after being fastened about the packaging closed end 38 (described below). In a further alternative embodiment, such plane of material 150 may include upon its back wall facing surface, a pressure sensitive adhesive for further securement/adjustment of the band to the packaging.

In still other alternative embodiments, the band-fastener 20, 27, 28 may be formed from more resilient but bendable materials, such as for example bendable polymeric materials, metallic foils, metallic wire ties (enclosed in polymeric or paper casings, as are commonly used for twist ties on gardening or waste-disposal bag applications) or a combination thereof. Such resilient but bendable materials may provide additional desirable closure benefits to the packaging, such as the ability of the band-fastener 20 to be changed in its effective-width dimension (shortened by being partially folded over itself and maintaining such shorter folded dimension) in order to accommodate a reduced amount of individually-wrapped absorbent articles in the packaging 10, and/or also to maintain a tightly secured packaging 10.

If the band-fastener 20, 27, 28 is non-integral with the flap wall 19, it may be bonded to the flap wall 19 at the lateral-most edge regions 20A, 20B by traditional bonding methods, such as by ultrasonic, adhesive, thermal, stitching, or staple bonding techniques. While such non-integral, band-fastener embodiments may offer benefits such as elasticity, stretchable, or bendable but rigid functionality, the manufacturing complexity and costs may be increased over integrally formed embodiments.

While processes are not specifically illustrated in the figures, it should be appreciated that if the band-fastener 20 is formed from the same material as the flap wall 19 (and integral with it), such band-fastener 20 may be formed from placement of a slit or puncture in the flap wall 19, adjacent the to-be-formed outermost flap wall edge 21, such that a spatial gap 23 is created. By ending the slit short of the lateral-most side edges of the packaging flap 31, connection points can be created thereby holding the band-fastener 20 to the flap wall 19. It should also be appreciated that certain of the packaging designs are more easily produced at greater speeds than others. For instance, those packaging flap designs illustrated in FIGS. 2A, 2B, 2C, and 2E include more rectangular-shaped packaging flaps 18 (with more rectangular shaped or slotted spatial gaps, such as those in FIGS. 2A and 2E), and would therefore be more efficiently produced than the more slanted packaging flap (and trapezoidal-shaped spatial gap of FIG. 2D). Such rectangular designs would produce less material waste for example. Similarly, packaging 10 without wider portions along the packaging length dimension would be more efficiently manufactured with less material waste. Packaging with frangible seams 57 may be produced with relatively reduced material waste as well, when compared with packaging of varied widths.

As seen in the front perspective view illustrated in FIG. 3, an alternative embodiment of a generally flattened, but opened packaging 10 in accordance with the invention includes an opening 61 leading to the pocket component 12, which opening 61 is fully contained within the front wall 14. The back wall 13 can be viewed through the opening 61. The edge 50 defines the oval-shaped opening that is situated beneath the seam 60. In the illustrated embodiment, the seal line features also extend along the seam 60 so as to provide additional support to the overall packaging structure.

The series of illustrations in FIGS. 4A-4C show front perspective views of various embodiments of the packaging 10 in their respective closed configurations. For example, in FIG. 4A, the opened packaging 10 of FIG. 1A is shown in its closed format. In the closed format, the packaging flap 18 has been folded about the seam 60 according to directional arrow 86, and the packaging closed end 38 has been slid between the flap wall outermost edge 21 and the band-fastener flap-facing inner edge 22 along the directional line 91. The band-fastener 20 (between attachment points at lateral-most edge regions 20A, 20B) in the packaging 10 can be seen in phantom lines behind the packaging closed end 38. This closed configuration is the configuration that is to be normally used by consumers while transporting articles in the packaging 10 within their pockets or purses. Should an article be needed, the packaging flap 18 is then pulled off of the packaging closed end 38 along the direction indicated by directional arrows 90. The packaging flap 18 is then extended, and the article is pulled from the opening 61 in the pocket component 12. The packaging flap 18 is then repositioned in its closed position between the integrally formed band-fastener 20, flap-facing inner edge 22 and the flap wall outermost edge 21, in order to preserve the cleanliness of the unused articles and to keep them from falling from the opening in the pocket component 12 of the packaging 10.

In FIG. 4B, an embodiment of a closed, band-fastened packaging 10 is illustrated having an elastic band-fastener 27 (in phantom lines behind the packaging closed end 38). As seen in the Figure, the elastic band-fastener 27 is maintained in place about the closed end (adjacent the back wall 13) from both the elastic compression of the elastic band-fastener 27 and the friction between the material of the elastic band-fastener 27 and the back wall 13. The elastic band-fastener 27 may be adjusted along the length of the back wall (such that it lies either closer to the packaging closed end 38 or closer to the portion of the back wall 13 adjacent the opening).

In FIG. 4C, an embodiment of a closed, band-fastened packaging 11 with extended-length band-fastener 28 is illustrated, having a packaging flap 18 for positioning over a front wall 14. The packaging 11 includes relatively thick side walls 115 and a bottom wall 116 (including its own seam). The packaging 11 has a relatively large expanded thickness T2, compared to previous embodiments. The packaging flap 18 is folded about a seam (acting as a fold line) 60 in accordance with directional arrow 110. The extended-length band-fastener 28, similar to that shown in FIG. 2D, is of an extended length such that a large spatial gap is present between the band-fastener 28, flap-facing inner edge 22 and the outermost flap wall edge 21. As a result, the extended-length band-fastener 28 can be easily placed about the packaging closed end 38 such that the packaging 11 can accommodate a relatively larger number of absorbent articles or a lesser amount of thicker articles, such as for example adult incontinence care absorbent inserts or garments. The relatively large spatial gap noted above also allows the packaging 11 to be carried by the extended-length band-fastener 28 when the packaging 11 is in an opened and fully extended configuration. If such usage is contemplated, it is desirable that such extended-length band-fastener 28 be strong enough to allow for the carrying of heavier absorbent articles. Such strength may be provided by additional basis weight of construction material in the band-fastener 28, additional strength bonded regions attaching the band-fastener 28 to the flap wall 19 (19B), the selection of more durable construction material for the band-fastener 28 (and or flap wall) or the base where the band-fastener 28 meets the flap wall, or a combination thereof. The extended-length band-fastener design 28 allows for a thicker overall packaging 10, without the necessity of using elastic or extensible construction materials in the band-fastener 28. Such band-fastener 28 relies on the band-fastener shape and the thicker packaging closed end 38 to keep the packaging flap 18 in place following packaging closure.

Figure 5A:
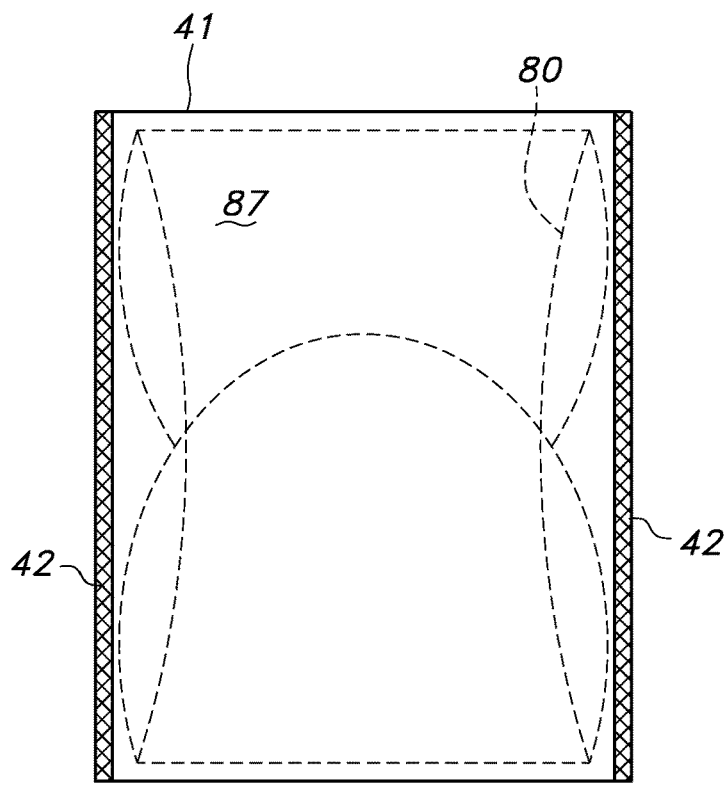
FIG. 5A illustrates an exemplary individually-wrapped absorbent article in the form of a folded panty liner (shown in phantom lines), that may be stored in a band-fastened convenience packaging in accordance with the invention.
Figure 5B:
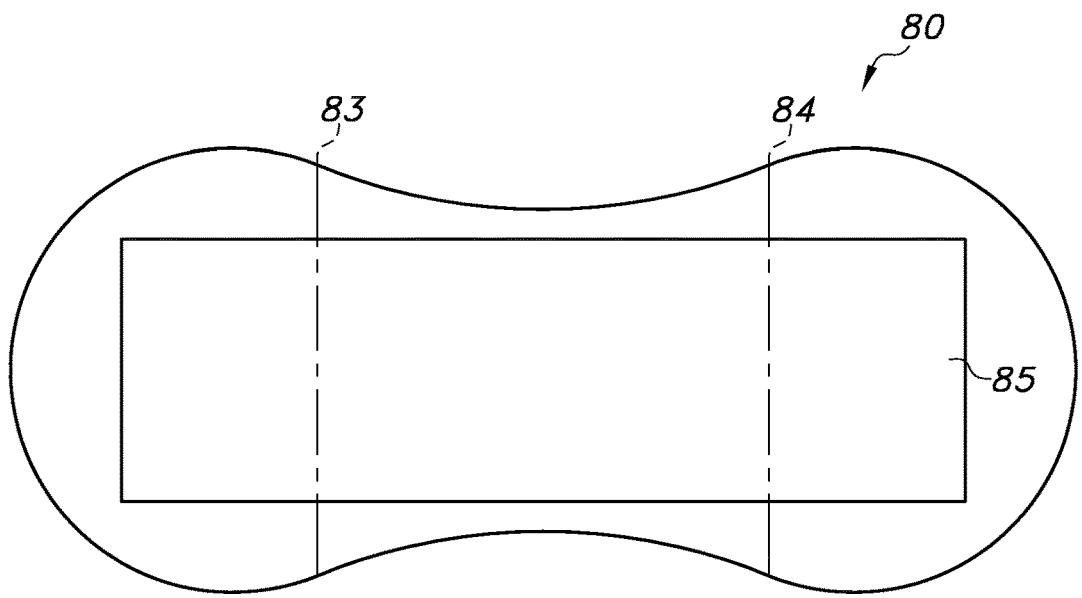
FIG. 5B illustrates a bottom plan view of an unfolded absorbent article in the form of a panty liner, that may be stored in a band-fastened convenience packaging in accordance with the invention.

The individually-wrapped absorbent articles 40, 51 contained in such packaging 10, 11 may encompass a wide variety of articles, including articles designed for feminine hygiene and/or adult incontinence care. While other article types are considered to be within the scope of the invention, only feminine care panty liners are illustrated for ease of reference. Folded feminine care panty liners 80 for placement in the crotch region of a consumer's undergarment, typically include a liquid permeable topsheet layer, a liquid impermeable backsheet layer, and an absorbent core layer sandwiched there-between (all not shown, but which are generally known in the absorbent article art). The panty liner 80 also typically includes garment attachment adhesive (not shown) that is covered with a protective release sheet 85 until the article is to be used (FIG. 5B). The exemplary panty liner 80 includes two fold lines 83, 84, although one or more numerous fold lines are also contemplated. The individual folded panty liner 80 is desirably placed within an individual wrapper 87 such that the folded edges of the panty liner 80 are either generally parallel with a sealed edge 42 of the wrapper or generally perpendicular to a sealed edge 42 (as shown). In the illustrated embodiment, the wrapper 87 includes two opposing sealed edges 42 and two opposing folded edges 41. The wrapper may also include only one sealed edge 42, three sealed edges, or four sealed edges as desired. Such sealing may be accomplished by thermal, adhesive, ultrasonic, pressure, needlepunching/stitching, staple, or other generally known bonding techniques, or combinations thereof. The absorbent articles or individually-wrapped absorbent articles as the case may be, may in one embodiment number between 2 and 20 in the packaging 10, 11, alternatively, between 4 and 20, alternatively, between 4 and 10, alternatively number 5, 6, or 7 to correspond to either the "work" week (depending on country) or "full" week. The absorbent articles contained within the packaging 10 may all be the same in one embodiment, or may alternatively vary by aesthetics (color, printed design, outer shape profile), functionality, or product type. For example, each of the articles within the packaging 10 may vary by aesthetics in order to personalize the consumer's experience with the absorbent articles over a day or a few days, or to provide an emotional benefit to the consumer so as to correspond to their particular daily moods. As another example, such absorbent articles may vary by type or functionality, such as by size (i.e. regular, long, overnight) or absorbency characteristics, such as by providing for light or heavy menstruation days, or light or heavy incontinence protection.

The packaging 10, 11 may include aesthetics or coloration so as to provide visual emphasis of the pocket component 12, the band-fastener 20, operation of the band-fastener closure mechanism, or a combination thereof. Such visual emphasis may highlight the features so as to assist the consumer in use of the band-fastener 20, 27, 28, or in the withdrawing of individual absorbent articles or individually-wrapped absorbent articles 40, 51 from the pocket component 12. For example, the color of the front wall 14 may be different from that of the back wall 13. The color of the band-fastener 20 may be different from the rest of the packaging flap 18, or from the overall packaging 10,11. The color of the pocket component 12 or opening edge 50 may be different from the remainder of the packaging 10. Other visual cues, such as directional arrows (not shown), color gradations, and visual designs that direct the consumers' focus or attention along one direction, may be strategically placed besides the band-fastener 20, 27, 28 so as to help facilitate movement of and removal of the band-fastener from about the packaging closed end 38, or instead, the securement (closure) of the band-fastener about the packaging closed end after the packaging has been opened. Such visual aesthetics can also help consumers in locating the band-fastener and to provide assurance that such packaging flap 18 is securely closed (such as by viewing the band at a location across the back wall of the packaging). In one embodiment, color markings may also be placed along the back wall 13 (outer-facing surface) to assist the consumer, by providing suggested placement locations for the band-fastener 20,27,28 along the back wall. Further, such packaging and/or packaging flap may also include brand markings.

Desirably in one embodiment, the packaging 10, 11 (including the packaging flap 18) is opaque and/or colored so as to prevent a passerby from easily observing the contents of the packaging 10, 11. Such opacity desirably prevents a passerby with normal (20/20) vision or corrected (20/20) vision from identifying the contents of the closed and covered packaging (that is covered with flap) from a distance of at least 1 meter, desirably at least 10 cm. Alternatively, such packaging or flap is transparent or translucent (such as from a transparent or translucent film) so that individual wrappers of individually-wrapped articles in the packaging can be seen through the transparent packaging or flap, but the articles remain obscured by the individual wrappers.

In further embodiments (not shown), additional closure mechanisms may be used in conjunction with the band-fastener 20, 27, 28 to provide additional securement of the packaging flap over the pocket component 12. Such additional closure mechanisms may also allow for the adjustment of the packaging flap. For instance, traditional tie knot mechanisms, mechanical hook and loop fasteners or patches of adhesive can be used as desired to further secure the packaging flap in place once it is placed around the packaging closed end 38. If such additional closure mechanisms are employed, they can include adhesive patches along the surface of the band-fastener that contacts the packaging back wall.

The packaging 10, 11 (and band-fastener) is desirably formed from a flexible sheet material that allows the packaging walls and flap to encircle the contents of the packaging and for the flap to easily fold about a seam for closure. Further, the packaging flap 18 and/or band-fastener 20 is desirably formed from a stretchable or elastic material (such as the same material) so as to easily allow the band-fastener to be placed about the packaging closed end 38.

In this fashion, a packaging design is described that allows for the repeated opening and secure closure of a portable, "convenience" style packaging. Such packaging utilizes generally a structure in which a packaging portion, such as the packaging closed end, is inserted like a tab, into an opening formed between a band-fastener and a packaging flap wall outermost edge. The band-fastener is attached at least at two separated points, to the packaging flap wall outermost edge. Such packaging stays in a closed configuration as a result of the packaging closed end either being compressed by the band-fastener, the friction or contact of the packaging closed end against the band-fastener, or a combination thereof. An integrated construction of the band-fastener and packaging flap from a single material (such as by forming an elongated opening via a slitting, aperturing or puncturing operation to create two separated portions of the flap) reduces material waste in manufacturing, and provides for a simpler manufacturing process than would otherwise be required with use of an adhesive tab or other nonintegral closure mechanism.

The packaging is opened by removal of the packaging closed end from the opening (between the band-fastener and flap wall outermost edge) and lifting up of the flap away from an underlying pocket component in the packaging. The opening (or spatial gap) formed between the band-fastener and flap wall outermost edge should be sized and configured to allow for the easy insertion of the packaging closed end into the opening, once the flap is folded into position. The packaging is closed by reversing the above described opening operation steps.

Such packaging utilizes at least in one embodiment, the base construction materials of the packaging for closing the packaging, rather than additional, more expensive closure mechanisms. Such packaging does not rely on adhesive to reseal a flap, and consequently, does not risk losing its sealing capability over time, or the inadvertent sticking of replacement articles as they are restocked by consumers in the packaging. The band-fastener packaging allows for repeated opening and secure closing of the packaging in various environments, without risk of loss of effective closure that might result from exposure to contaminants or moisture in a consumer's environment.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A band-fastened packaging for containing absorbent articles, said band-fastened packaging have a longitudinal dimension, a width dimension and a thickness dimension, comprising:
    a pocket component for housing absorbent articles, said pocket component including at least a front and back wall, with at least said front wall defining an opening into said pocket component and at least said front and back walls forming a packaging closed end,
    a packaging flap hingedly connected to said back wall for folding over said opening, said packaging flap including a flap wall having an outermost flap wall edge,
    a band-fastener attached to said outermost flap wall edge at least at two spaced-apart attachment points, said band-fastener capable of separating from said outermost flap wall edge between said at least two spaced-apart attachment points, and including a flap-facing inner edge, such that the packaging closed end may be inserted between said two spaced-apart attachment points and also between said outermost flap wall edge and said band-fastener flap-facing inner edge, whereby said packaging flap may be held in place adjacent said packaging closed end in order to maintain said opening covered by said packaging flap until an absorbent article contained within said band-fastened packaging is desired for use.

2. The band-fastened packaging of claim 1, wherein said band-fastener is attached to said outermost flap wall edge along a frangible seam selected from the group consisting of a line of perforation, line of weakness, and a combination thereof.

3. The band-fastened packaging of claim 1, wherein said band-fastener is separated from said outermost flap wall edge by a distance of between about 1 and 10 mm, thereby forming a spatial gap between said two attachment points, and between said outermost flap wall edge and said band-fastener flap-facing inner edge.

4. The band-fastened packaging of claim 1, wherein said band-fastener is formed from either a stretchable material, an elastic material, a tissue material, a metal, or a polymeric material.

5. The band-fastened packaging of claim 1, wherein said front wall entirely defines said opening.

6. The band-fastened packaging of claim 1, wherein said front wall and back wall have two different lengths.

7. The band-fastened packaging of claim 1, wherein said band-fastener includes a width dimension and includes a sealed edge along its full width dimension.

8. The band-fastened packaging of claim 1, wherein said back wall is integral with said flap wall.

9. The band-fastened packaging of claim 1, wherein said band-fastener is integral with said flap wall.

10. The band-fastened packaging of claim 9, wherein said band-fastener is of uniform length across its entire width dimension.

11. The band-fastened packaging of claim 1, further including individually-wrapped absorbent articles contained within said pocket component, wherein said individually-wrapped absorbent articles are folded absorbent articles that are wrapped in wrappers having two opposing sealed edges and two opposing folded edges, and further wherein said individually-wrapped absorbent articles are placed within said band-fastened packaging such that said wrapper sealed edges are parallel with said band-fastened packaging longitudinal dimension.

12. The band-fastened packaging of claim 1, further including individually-wrapped absorbent articles contained within said pocket component, wherein said individually-wrapped absorbent articles number between 2 and 20.

13. The band-fastened packaging of claim 12, wherein at least one of said individually-wrapped absorbent article varies from another individually-wrapped absorbent article, based on either article size, article absorbency, article aesthetics, or article type.

14. The band-fastened packaging of claim 1, wherein said pocket component and said packaging flap are formed of substantially opaque materials such that contents contained within said pocket component which opening is covered by said packaging flap are not capable of article-type identification by a consumer with 20/20 vision, when viewing the packaging from a distance of one meter away.

15. The band-fastened packaging of claim 1, wherein said band-fastener is of an elongated length.

16. The band-fastened packaging of claim 1, wherein said band-fastener is formed of an elastic material.

17. The band-fastened packaging of claim 1, wherein said band-fastener, said outermost flap wall edge, and peripheral side edges of said band-fastened packaging each include ultrasonic bond areas.

18. The band-fastened packaging of claim 1, wherein said front and back walls both define said opening.

19. The band-fastened packaging of claim 1, wherein said band-fastener includes upon its surface a secondary closure mechanism selected from the group consisting of adhesive, a tie knot, and a hook or loop fastener.

20. The band-fastened packaging of claim 1, wherein said packaging includes a transparent or translucent portion, such that individual wrappers of individually-wrapped articles contained within said band-fastened packaging can be seen through said transparent or translucent portion.

* * * * *